(12) United States Patent
Muller et al.

(10) Patent No.: US 6,293,938 B1
(45) Date of Patent: Sep. 25, 2001

(54) PHOTO-REFRACTIVE KERATECTOMY

(75) Inventors: David F. Muller, Boston; Mike D'Agati, Brighton; Marc Friedman, Watertown, all of MA (US); Troy Harmon, Landsdale, PA (US); Peter Klopotek; Alex Sacharoff, both of Framingham, MA (US); Evan Sherr, Wellesley, MA (US)

(73) Assignee: Summit Technology, Inc., Waltham, MA (US)

( * ) Notice: Subject to any disclaimer, the term of this patent is extended or adjusted under 35 U.S.C. 154(b) by 0 days.

(21) Appl. No.: 08/695,115

(22) Filed: Aug. 8, 1996

Related U.S. Application Data

(63) Continuation of application No. 08/224,830, filed on Apr. 8, 1994, which is a continuation of application No. 08/563,184, filed on Nov. 27, 1995.

(51) Int. Cl.$^7$ .................................................. A61F 9/08
(52) U.S. Cl. .................... 606/5; 606/3; 606/10; 606/13; 128/898
(58) Field of Search ............................. 606/3–7, 10–18; 128/898

(56) References Cited

U.S. PATENT DOCUMENTS

| | | |
|---|---|---|
| 4,733,944 | 3/1988 | Fahlen et al. . |
| 4,856,513 | 8/1989 | Muller . |
| 4,941,093 | 7/1990 | Marshall et al. . |
| 4,988,348 | * 1/1991 | Bille .......................................... 606/5 |
| 4,994,058 | 2/1991 | Raven et al. . |
| 5,019,074 | 5/1991 | Muller . |
| 5,091,626 | 2/1992 | Lewis et al. . |
| 5,163,934 | 11/1992 | Munnerlyn . |
| 5,741,245 | * 4/1998 | Cozean et al. ........................... 606/5 |

FOREIGN PATENT DOCUMENTS

| | | |
|---|---|---|
| 0 080 597 | 12/1986 | (EP) . |
| 2 180 363 A | 3/1987 | (GB) . |
| WO 87/06126 | * 10/1987 | (WO) . |

OTHER PUBLICATIONS

Bor et al., "Physical Problems of Excimer Laser Cornea Ablation", *Optical Engineering* 32: 2481–2486 (1993).
Bruno, et al., "Laserbeam Shaping for Maximum Uniformity and Minimum Loss," *Lasers & Applications*, 91–94 (Apr. 1987).
Deng, et al., "Uniform Illumination of Large Targets Using a Lens Array," *Applied Optics* 25: 377–381 (1986).
emphasis™ Erodible Mask brochure (May, 1993).
Grojean, et al., "Production of Flat Top Beam Profiles for High Energy Lasers,"*Rev. Sci. Instrum.* 51:375–376 (1980).

(List continued on next page.)

*Primary Examiner*—David M. Shay
(74) *Attorney, Agent, or Firm*—Thomas J. Engellenner; Tram Anh T. Nguyen; Nutter, McClennen & Fish, LLP

(57) ABSTRACT

The invention features improvements in PRK procedures that relate to preventing non-uniform removal of material from the corneal surface. It has been realized that photoablation by-products resulting during the PRK procedure can affect the accuracy and the predictability of the procedure. Under certain conditions, the plume of photoablation by-products that have left the corneal surface can non-uniformly redeposit onto the ablation area and thus affect the uniformity of subsequent material removal. The plume of photoablation by-products, in the space above the corneal surface, can also non-uniformly affect the escape of further photoablation products from the surface. In addition to the plume effects, it has been realized that the hydration level of the corneal tissue during the PRK procedure can vary over the ablation area and likewise non-uniformly affect the PRK procedure.

26 Claims, 14 Drawing Sheets

OTHER PUBLICATIONS

Han, et al., "Reshaping Collimated Laser Beams with Gaussian Profile to Uniform Profiles," *Applied Optics* 22:3644–3647 (1983).

Horton, et al., "Design of a Specular Aspheric Surface to Uniformly Radiate a Flat Surface Using a Nonuniform Collimated Radiation Source," *Journal of Heat Transfer*, 453–458 (Nov. 1972).

Iwasaki, et al., "Flattening Laserbeam Intensity Distribution," *Lasers & Applications*, 76–78 (Apr., 1983).

Krueger, et al., "Corneal Surface Morphology Following Excimer Laser Ablation with Humidified Gases," *Arch Opthalmol* 111: 1131–1137 (1993).

Lacombat, et al., "Laser Projection Printing," *Solid State Technology*, 115–121 (Aug., 1980).

Morrill, "Theories Presented on PRK's 'Central Islands'," *Ocular Surgery News*, 26–27 (Sep. 15, 1993).

Ozaki, et al., "Cylindrical Fly's Eye Lens for Intensity Redistribution of an Excimer Laser Beam," *Applied Optics* 28: 106–110 (1989).

Piebenga, et al., "Excimer Photorefractive Keratectomy for Myopia," *Opthalmology* 100: 1335–1345 (1993).

Rhodes, et al., "Refractive Optical Systems for Irradiance Redistribution of Collimated Radiation: Their Design and Analysis," *Applied Optics* 19:3545–3553 (1980).

Tabat, et al., "Profile Characteristics of Excimer Laser Micromachined Features," *SPIE* 1835:144–157 (1992).

Wright, "Corneal Islands Minimized by Latest Refinements," *Opthalmology Times*, (Sep. 15, 1993).

International Search Report PCT/US95/04177.

International Search Report for PCT/US95/04177.

Bor et al., "Physical problems of excimer laser cornea ablation", *Optical Engineering*, 32:2481–2486 (Oct. 1993).

Morrill, "Theories presented on PRK's 'central islands'", *Ocular Surgery News*, pp. 26–27 (Sep. 15, 1993).

Wright, "Corneal Islands Minimized by Latest Refinements", *Opthalmology Times*, (Sep. 15, 1993).

Piebenga, et al., "Excimer Photorefractive Keratectomy for Myopia", *Opthalmology*, 100:1335–1345 (Sep. 1993).

Krueger, et al., "Corneal Surface Morphology Following Excimer Laser Ablation with Humidified Gases", *Arch Opthalmol*, 111:1131–1137 (Aug. 1993).

Tabat et al., "Profile characteristics of excimer laser micromachined features", *SPIE*, 1835:144–157 (1992).

Ozaki et al., "Cylindrical fly's eye lens for intensity redistribution of an axcimer laser beam", *Applied Optics*, 28:106–110 (Jan. 1989).

Bruno et al., "Laserbeam Shaping for Maximum Uniformity and Minimum Loss", *Lasers & Applications*, pp. 91–94 (Apr. 1987).

Deng, et al., "Uniform illumination of large targets using a lens array", *Applied Optics*, 25:377–381 (Feb. 1986).

Iwasaki et al., "Flattening Laserbeam Intensity Distribution", *Lasers & Applications*, pp. 76–78 (Apr. 1983).

Han et al., "Reshaping collimated laser beams with Gaussian profile to uniform profiles", *Applied Optics* 22:3644–3647 (Nov. 1983).

Rhodes et al., "Refractive optical systems for irradiance redistribution of collimated radiation: their design and analysis", *Applied Optics*, 19:3545–3553 (Oct. 1980).

Lacombat et al., "Laser Projection Printing", *Solid State Technology*, pp. 115–121 (Aug. 1980).

Grojean et al., "Production of flat top beam profiles for high energy lasers", *Rev. Sci. Instrum.*, 51:375–376 (Mar. 1980).

Horton et al., "Design of a Specular Aspheric Surface to Uniformly Radiate a Flat Surface using a Nonuniform Collimated Radiation Source", *Journal of Heat Transfer*, pp. 453–458 (Nov. 1972).

emphasis™ Erodible Mask brochure (May 1993).

* cited by examiner

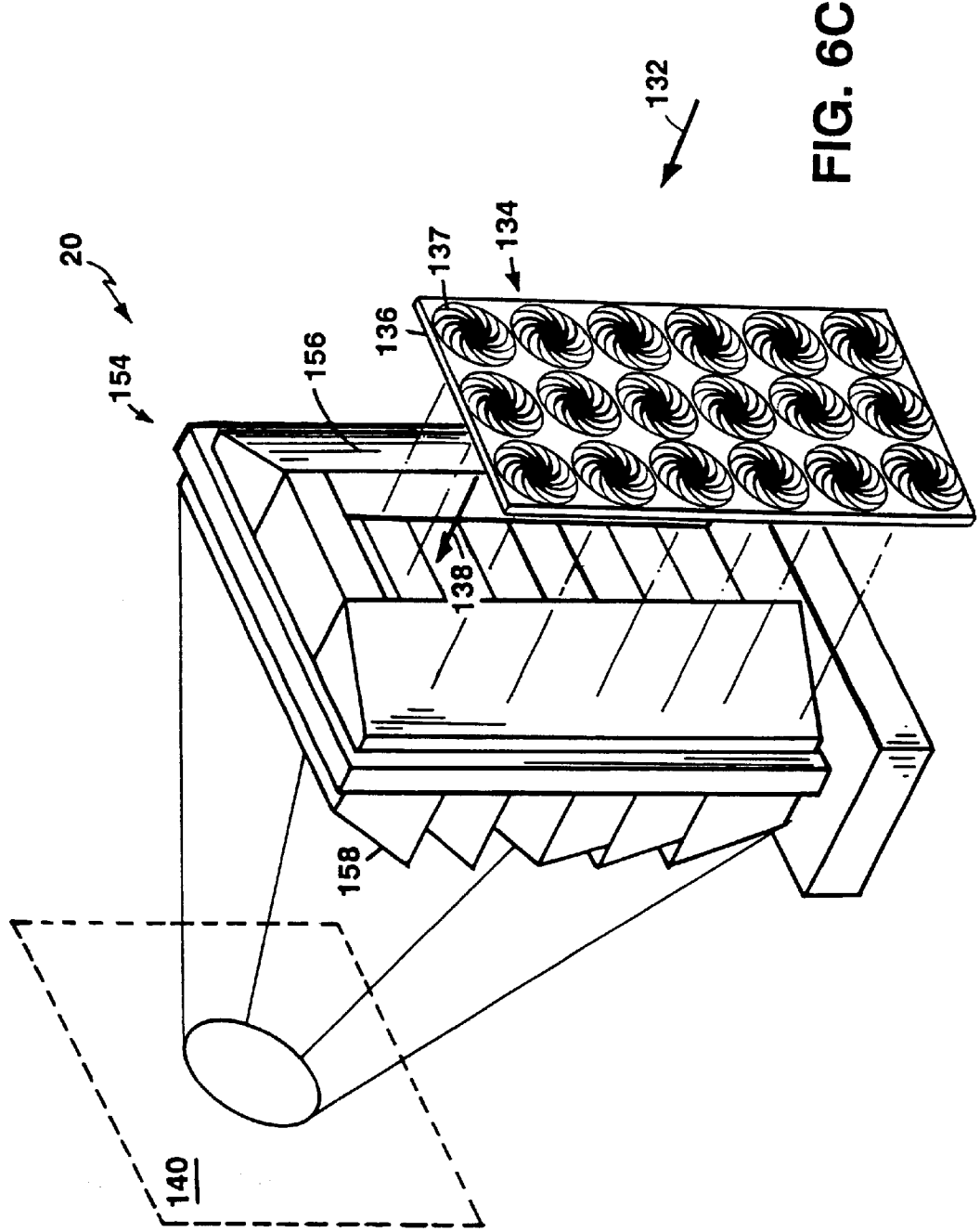

PHOTO-REFRACTIVE KERATECTOMY

This application is a continuation of application Ser. No. 08/224,830 filed on Apr. 8, 1994 Entitled: PHOTO-REFRACTIVE KERATECTOMY, which is a continuation of Ser. No. 08/563,184 filed Nov. 27, 1995, abandoned.

BACKGROUND

This invention relates to improvements in photo-refractive keratectomy (PRK).

PRK involves the removal of corneal tissue in a controlled fashion to shape the surface of the cornea to change the radius of curvature, or refractive power, of a patient's eye to treat e.g., myopia or hyperopia.

The cornea comprises transparent avascular tissue that forms the anterior portion of the eye. The cornea functions as both a protective membrane and a "window" through which light passes as it proceeds to the retina. The transparency of the cornea is due to its uniform structure, avascularity, and deturgescence, which is the state of relative hydration of the corneal tissue. The average adult cornea is about 0.65 mm thick at the periphery, and about 0.54 mm thick in the center. From anterior to posterior, the cornea has the following five distinct layers: the epithelium, Bowman's membrane, the stroma, Descemet's membrane, and the endothelium. The present invention concerns the epithelium, Bowman's membrane, and the stroma. The epithelium consists of five or six layers of cells, and the underlying Bowman's membrane, a clear acellular layer, is a modified portion of the stroma. The corneal stroma accounts for about 90 percent of the corneal thickness.

A major proportion of the refractive power of the eye is determined by the curvature of the anterior surface of the cornea, so that changing the shape of the cornea offers a way to significantly reduce a refractive problem in the eye.

Various techniques have been proposed for shaping the cornea of a patient's eye. The general technique involves removing the epithelium, and then shaping the underlying Bowman's and stroma layers, either surgically, or by using photoablation with e.g., ultraviolet radiation from an excimer laser or infrared laser radiation from an infrared laser operating at a wavelength of about 2.9–3.2

One technique, described in Muller, U.S. Pat. No. 4,856,513 (assigned to the present assignee), uses a laser and an erodible mask. The mask, with a predefined profile of resistance to erosion by laser radiation, is disposed between the laser and the corneal surface. A portion of the laser radiation is absorbed by the mask, while another portion is transmitted to the corneal surface in accordance with the mask profile, thereby selectively photoablating the corneal surface into a desired shape.

In another technique, described in Marshall et al., U.S. Pat. No. 4,941,093 (assigned to the present assignee), the shape and size of the area of the corneal surface irradiated by laser energy is selected and controlled so that some areas of the corneal surface become more eroded than others and a desired corneal shape is achieved.

While the PRK procedure has already reached a clinically accepted level, the possibility of achieving even better results has been somewhat elusive. The present invention provides a new level of insight into conditions that can occur in PRK and provides techniques that address these conditions to enable enhanced predictability, stability, and safety of the procedure to be achieved.

SUMMARY

According to the invention it has been realized that under particular conditions various phenomena may occur.

It has been realized that photoablation by-products resulting during the PRK procedure can affect the accuracy and the predictability of the procedure. Under certain conditions, the plume of photoablation by-products that have left the corneal surface can non-uniformly redeposit onto the ablation area and thus affect the uniformity of the result. The plume of photoablation by-products, in the space above the corneal surface, can also non-uniformly affect the escape of further photoablation products from the surface. In addition to the plume effects, it has been realized that the hydration level of the corneal tissue during the PRK procedure can vary over the ablation area and likewise non-uniformly affect the PRK results.

One cause of non-uniform tissue removal is non-uniform redeposition of ablation by-products during the PRK procedure. Typical PRK procedures employ substantially flat (i.e., uniform) laser beam intensity profiles to shape the corneal surface. The inventors have discovered that under such conditions, the beam pulses impinging on the corneal surface can cause photoablation by-products in the form of a plume to redeposit onto the corneal surface in a manner causing non-uniform removal of material. The rapid expansion of the ablation products away from the surface of the eye caused by conventional PRK conditions may create a relatively decreased pressure in the space above a central portion of the ablation region at the eye surface and a relatively higher pressure in the space near the edges of the ablation region. Such conditions can produce a plume action that can cause non-uniform redeposition onto the ablation area. The particular manner in which the ablation products deposit onto the surface of the ablation area depends upon a number of factors. Under conventional PRK conditions, the ablation products may preferentially deposit in the central region of the ablation area, thereby creating a central island of excess material. Also, the deposited material can act as e.g., a mask, or radiation absorber, that interferes with further corneal tissue ablation. The non-uniform distribution of ablation products on the surface of the ablation area can cause a corresponding non-uniform shape to become transferred into the patient's cornea with each successive photoablative pulse.

Another cause of non-uniform tissue removal is plume interference with either beam delivery or escape of the ablation by-products from the surface of the ablation area. Under conventional PRK conditions, the dynamics of the plume of ablation by-products can cause less material to be removed from central portion of the ablation area than from the surrounding portion. For example, the region just above the central portion of the ablation area appears to provide a less effective escape path for gaseous ablation by-products than the region above the periphery of the ablation area.

The non-uniform removal of corneal material tends to cause a surgeon performing a PRK procedure to shape a patient's cornea in a manner outside of the planned correction, which is usually selected based upon a predetermined assumption of a uniform depth of ablation per pulse. Non-uniform shaping of the patient's eye could cause the patient discomfort and possibly a loss in visual acuity.

As mentioned above, the variation in the hydration level of the corneal tissue across the surface of the ablation area can also cause non-uniform ablation. The cornea includes a major proportion of fluid. The inventors have discovered that, as corneal tissue is ablated during a PRK procedure, fluids can accumulate in the ablated areas of the cornea and non-uniformly alter the photoablation sensitivity of the corneal tissue across the surface of the ablation area, and thereby cause non-uniform ablation of the cornea.

Thus the inventors have discovered that the PRK procedure may be further refined by novel steps that substantially control, or avoid, the above-mentioned phenomena.

In one general aspect, the invention features a PRK system for producing a desired refractive correction in an ablation area in the cornea of a patient's eye comprising a source of an initial beam of photoablating radiation capable of ablating the cornea of a patient's eye during a PRK procedure, and means for modifying a plume of ablation products resulting from photoablation of the patient's cornea, the modifying means being constructed and arranged to alter formation dynamics of the plume in a manner substantially preventing the plume from causing non-uniform ablation of the patient's cornea.

According to one aspect, the invention features a PRK system wherein the plume modifying means comprises means for removing material that leaves the surface of the ablation area in a manner substantially preventing a plume of ablation products produced by the photoablating radiation from causing non-uniform ablation of the patient's cornea.

In certain preferred embodiments, the plume-altering means preferably comprises an apparatus for producing a plume-altering flow of humidified gas, the apparatus having an orifice for delivering the flow of humidified gas to the ablation area at a velocity sufficient to substantially prevent non-uniform ablation of the patient's cornea.

The velocity of the humidified gas at the surface of the ablation area is preferably greater than about 1 m/s. The orifice is preferably arranged about 1 to 5 cm from the ablation area and the velocity of the humidified gas at the orifice is at least about 100 meters per second. The orifice is preferably arranged to deliver the flow of humidified gas to the ablation area at an angle in the range of about 0 to 30 degrees relative to an axis normal to the surface of the ablation area. In a preferred embodiment, the apparatus is constructed to provide the humidified gas as a continuous flow. In another preferred embodiment, the apparatus is constructed to provide the humidified gas as a series of intermittent puffs of the gas, the puffs being delivered to the ablation area at times substantially synchronized with incidence of the photoablative radiation pulses upon the ablation area. In certain embodiments, the apparatus is preferably disposed to direct the humidified gas from only one side of the ablation area. In certain other preferred embodiments, the apparatus preferably comprises a nozzle assembly surrounding a significant portion of the ablation area, the nozzle assembly being arranged to simultaneously introduce the humidified gas to the ablation area from a plurality of different locations above the ablation area.

The nozzle provides a relatively inexpensive and non-obtrusive correction for reducing the non-uniform ablation caused by e.g., the re-entrance of ablation products to the surface of the ablation region, which would otherwise tend to occur without the application of the appropriate gas flow to the ablation region.

In another aspect, the invention features a PRK system comprising a beam modifier for producing a plurality of subbeams from the initial beam during the PRK procedure, the beam modifier being disposed between the source and the cornea of the patient's eye for separately modifying different subbeam portions of the initial beam to thereby create respective subbeams each having a respective predetermined modification, the predetermined modification being selected to create a resulting beam from the subbeams for ablating the patient's cornea having a desired cross-sectional intensity profile that substantially prevents ablation by-products resulting from photoablation of the patient's cornea from causing non-uniform ablation of the patient's cornea.

According to this aspect of the invention, auxiliary instrumentation for the modification of the plume may be omitted. In this instance, the formation of the plume is altered by the preselected profile of the photoablative radiation pulses. In such scheme, the photoablative radiation serves as both the corneal tissue ablation means and the plume-altering means, and thus embodies a self-regulating capability.

In a preferred embodiment according to this aspect, the beam modifier comprises a close-packed array of waveguides each constructed and arranged for separately receiving and guiding respective subbeam portions of the initial beam to respective portions of the ablation area in the patient's cornea.

In certain preferred embodiments, the PRK system further comprises a mask disposed between the source and the beam modifier, the mask having a predetermined profile of resistance to erosion by the photoablating radiation, the predetermined profile being selected to vary the total optical energy received across the surface of the ablation area during the PRK procedure in a manner producing the desired refractive correction in the patient's cornea.

In certain embodiments, the PRK system further comprises an optical beam shaping means disposed between the source and the beam modifier for optically varying the area of the corneal surface in the ablation area to which the photoablating radiation is delivered while maintaining in the photoablating radiation a substantially constant energy per unit area over the illuminated portions of the ablation area during the PRK procedure. The beam shaping means preferably comprises an iris having an aperture for shaping the beam by passage therethrough.

In preferred embodiments, the beam modifier comprises an intensity modifier for receiving the initial beam of photoablating radiation, the intensity modifier being constructed and arranged to separately modify the intensity profile of different subbeam portions of the initial beam to thereby create the respective subbeams each having the respective predetermined modification.

In another embodiment according to this aspect, the PRK system further comprises a subbeam-directing optical system constructed and arranged to direct the multiple subbeams along respective subbeam beam paths that substantially overlap in an overlap plane, whereby, a resulting beam of radiation is created at the overlap plane that has an intensity profile equal to the optical incoherent summation of the modified intensity profiles of the overlapping subbeams, the intensity profile of the resulting beam corresponding to the desired cross-sectional profile. As used herein, the term optical incoherent summation means that the intensity at any given location in the overlap plane results from an incoherent sum of the respective portions of the contributing subbeams, and that interference effects can be neglected. The intensity modifier preferably comprises an array of intensity-modifying profiling elements disposed across the initial beam each substantially producing a corresponding subbeam. Each of the profiling elements preferably comprises a predetermined pattern of radiation transmissive and non-transmissive regions. The patterns are preferably constructed and arranged to produce corresponding subbeams modified according to substantially identical intensity-modifying functions.

According to another aspect, the invention features a PRK system comprising an acoustic device disposed near the ablation area for producing localized acoustic-waves proximal to the ablation area in a manner substantially preventing a plume of ablation products produced by the photoablating radiation from causing non-uniform ablation of the patient's cornea.

In a preferred embodiment, the acoustic device is constructed and arranged to be activated at times synchronized with the incidence of the pulses of the photoablating radiation upon the surface of the ablation area. The acoustic device preferably comprises a shroud surrounding the ablation area, the shroud being constructed and arranged to produce an acoustic wave in the ablation area of the patient's cornea in a manner altering the formation dynamics of the plume of ablation products. The acoustic device is preferably constructed and arranged to produce an acoustic wave in the air proximal to the ablation area in a manner altering the formation dynamics of the plume of ablation products.

In another general aspect, the invention features a PRK system comprising means for controlling the relative hydration of the patient's cornea in a manner substantially preventing the corneal fluid dynamics in the ablation area from detrimentally affecting the photoablation of the patient's cornea during the PRK procedure.

In another preferred embodiment, the hydration controlling means comprises means for uniformly attenuating the cross-sectional intensity of the initial beam pulses, the attenuating means being constructed and arranged to provide intensity attenuation in the initial beam pulses. The intensity attenuating means is preferably constructed and arranged to attenuate the intensity of selected initial beam pulses below the intensity level required for corneal photoablation.

In certain preferred embodiments, the hydration controlling means comprises a source of pulses of infra-red radiation of a wavelength selected to correspond with a peak in the wavelength-absorption profile of water, the pulses of infrared radiation having an intensity selected to control water accumulation in the ablation area during the PRK procedure. The pulses of infra-red radiation preferably have a fluence of 1 mJ/cm$^2$ and have a wavelength between about 1 to 12 $\mu$m. The PRK system preferably further comprises an infra-red beam-shaping means for shaping the pulses of infra-red radiation, the shapes of the pulses being selected to substantially correspond to the central region of the ablation area. The hydration controlling means is preferably constructed and arranged to deliver the pulses of infrared radiation in a sequence that alternates with the initial beam pulses.

In some embodiments, the uniformity corneal hydration is controlled by applying controlled heating to the anterior surface of the patient's cornea by using a source of illumination having an intensity greater than about 10 mW cm$^{-2}$ and having a wavelength in a range selected to be preferentially absorbed by the top 100 $\mu$m of corneal tissue. In certain embodiments, drugs are applied to the cornea that reduce and regulate the release of corneal fluid during PRK.

In yet another preferred embodiment according to this aspect, the hydration controlling means comprises beam-shaping means for optically varying the area on the surface of the ablation area to which the profiled beam pulses are delivered from an initial area of a size substantially corresponding to the size of the ablation area to a final, relatively smaller size.

In certain embodiments, the beam-shaping means preferably comprises an iris for shaping the beam that passes through it. In certain other embodiments, the beam-shaping means preferably comprises a mask disposed between the source and the beam profiling means, the mask having a predetermined profile of resistance to erosion by the photoablating radiation, that corresponds to the correction desired to be made for the above effects.

In certain preferred embodiments, the hydration controlling means comprises means for saturating the ablation area with fluid in a manner maintaining a substantially uniform hydration level throughout the ablation area during the PRK procedure. The saturating means preferably comprises an apparatus for continuously misting the ablation area with water during the PRK procedure. In another embodiment, the saturating means preferably comprises a device for applying drops of water to the ablation area during the PRK procedure.

In another aspect, the invention features a method for producing a desired refractive correction in an ablation area in the cornea of a patient's eye comprising the steps of providing initial beam pulses of photoablating radiation capable of ablating the cornea of a patient's eye during a PRK procedure, profiling the cross-section of each of the initial beam pulses to produce a substantially predetermined ablation profile across the surface of the patient's cornea in the ablation area, and controlling the relative hydration of the patient's cornea in a manner substantially preventing the corneal fluid dynamics in the ablation area from affecting the photoablation of the patient's cornea during the PRK procedure.

In certain preferred embodiments, the hydration controlling step comprises uniformly attenuating the cross-sectional intensity of the initial beam pulses. The intensity attenuating step preferably comprises attenuating the intensity of certain of the initial beam pulses below the intensity level required for corneal photoablation.

In one preferred embodiment, the hydration controlling step comprises providing pulses of infra-red radiation of a wavelength selected to correspond with a peak in the wavelength-absorption profile of water, the pulses of infra-red radiation having an intensity selected to control water accumulation in the ablation area during the PRK procedure.

The method preferably further comprises the step of shaping the pulses of infra-red radiation, the shapes of the pulses being selected to substantially correspond to the central region of the ablation area.

In certain embodiments, the hydration controlling step preferably comprises delivering the pulses of infrared radiation to the ablation area in a timed sequence that alternates with the incidence of the initial beam pulses upon the surface of the ablation area.

In one preferred embodiment, the hydration controlling step comprises optically varying the area on the surface of the ablation area to which the profiled beam pulses are delivered from an initial area of a size substantially corresponding to the size of the ablation area to a final, relatively smaller size.

In another aspect, the invention features a method for producing a desired refractive correction in an ablation area in the cornea of a patient's eye comprising the steps of: providing initial beam pulses of photoablating radiation capable of ablating the cornea of a patient's eye during a PRK procedure; modifying the initial beam pulses to produce respective modified pulses having a modification selected, at least in part, based upon the initial shape of the patient's cornea, the desired refractive correction, and the ablation depth achieved by each of the modified pulses; applying the modified pulses to the ablation area of the patient's cornea; providing final beam pulses to produce respective final correction pulses for removal of non-uniformly ablated corneal tissue in the ablation area caused by interaction of the modified pulses with ablation by-products resulting from photoablation of the patient's cornea by the modified pulses, the modification of the final correction pulses being selected to remove concentration of the photoablation by-products onto the central region of the ablation area; and applying the final correction pulses to the ablation area of the patient's eye, whereby the desired refractive correction is achieved.

Other features and advantages will become apparent from the following description and from the claims.

BRIEF DESCRIPTION OF THE DRAWINGS

FIG. 6C is a perspective view of a subbeam-directing optical system including overlapping prisms.

DESCRIPTION OF THE PREFERRED EMBODIMENTS

Figure 1:
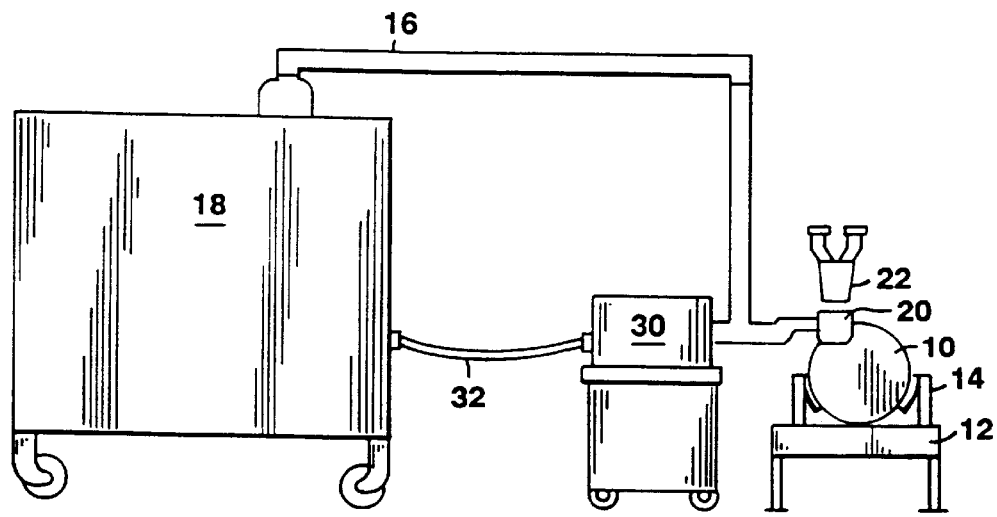
FIG. 1 is a side elevational view of a patient undergoing photoablative shaping of corneal tissue.

Referring to FIG. 1, a patient 10, lying on an operating table 12 with his head restrained between two side supports 14, is undergoing photoablative shaping of his cornea in a PRK procedure in accordance with the invention.

An optical support assembly 16 (e.g., a standard optical support obtainable from Laser Mechanisms of Bloomfield Hill, Mich. U.S.A.) supports beam delivery optics that transmit photoablative radiation from e.g., a laser source inside housing 18 to a correction device 20 that is constructed and arranged, as described in detail below, to correct a discovered tendency for conventional PRK procedure conditions to cause non-uniform ablation of the corneal tissue.

Correction device 20 is supported above a patient's eye by an eyepiece 22 (e.g., available from Steinway Instruments of San Diego, Calif. U.S.A). During the cornea shaping procedure, the patient's eye may be observed using a surgical microscope 24.

Figure 2:
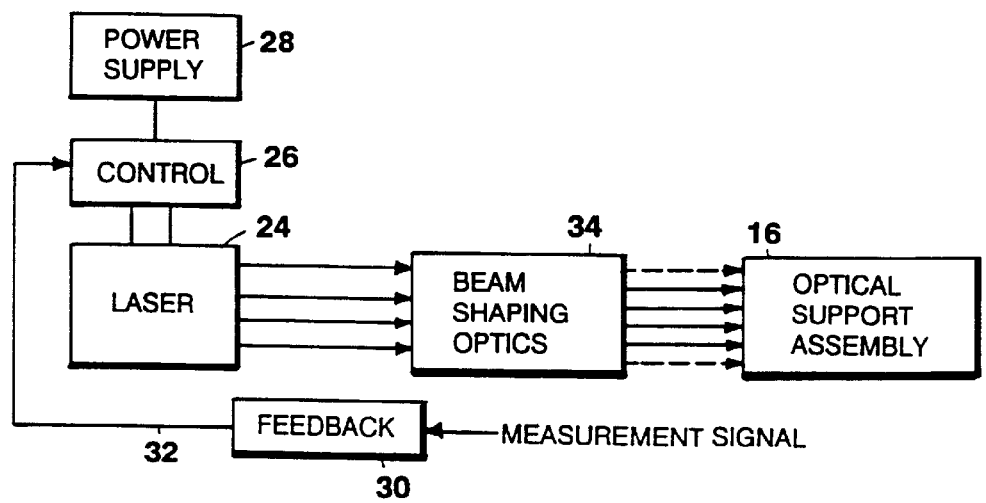
FIG. 2 is a schematic diagram illustrating the relationship between optical components inside a laser source and an optical support assembly.

As shown in FIG. 2, the laser source includes a laser 24 (e.g., an EXCIMED ArF excimer laser (193 nm) available from Summit Technology, Inc. of Watertown, Mass. U.S.A.; other lasers such as HF, pulsed $CO_2$, infrared lasers at wavelengths of about 2.6–3.1 $\mu$m, Er:YSGG and Er:YAG lasers may also be used) that is controlled by a controller 26 (e.g., a commercially available microprocessor-based computer), and powered by a power supply 28. Controller 26 selectively controls the frequency and intensity of radiant pulses from laser 24.

A feedback device 30, such as a profilometer or keratometer (e.g., a PHOTOKERATOSCOPE™ manufactured by Sun Contact Lens Company of Kyoto, Japan, or a CORNEASCOPE™ manufactured by International Diagnostic Instruments Limited, Broken Arrow, Okla. U.S.A.), sends signals to the controller via a feedback path 32, for precise control of the laser during the photoablation procedure.

Beam-shaping optics 34 provide a beam of a desired shape and dimension to an optical system housed within optical support assembly 16. The beam-shaping optics may not always be necessary, should the laser output beam be directly usable. However, with most lasers it will normally be desirable to perform some initial shaping of the beam. For example, some types of laser systems produce beams with rectangular cross-sections (e.g., excimer lasers) and it will normally be preferable to form the beams into square or circular cross-sections.

A typical excimer laser, operating at 193 nm, has a beam profile that is 8 mm by 24 mm with a gaussian cross section in the short dimension and a 10% variation from uniformity over most of the long dimension.

Suitable irradiation intensities vary depending on the wavelength of the laser radiation and the nature of the irradiated surface. For any given wavelength of laser radiation applied to the corneal layers, there is typically a threshold value of energy density below which significant ablation does not occur. Above this threshold density, there will be a range of energy density over which increasing energy densities provide increasing depths of ablation, until a saturation point is reached, above which no significant increase in ablation rate occurs.

Typically, to achieve corneal ablation, the laser system is used to provide an energy density at the corneal surface of slightly less than the saturation value. For example, when ablating the cornea with radiation having a wavelength of 193 nm, it is preferable to provide pulses of radiation that have energy densities of about 100–150 mJ cm$^{-2}$ per pulse. Typically, a single pulse which has this energy distribution will ablate a depth in the range of about 0.1–3 $\mu$m.

Wavelengths in the range of about 300 nm to about 1400 nm should not be used, as this radiation tends to penetrate the eye and damage the cells lying below the stromal layer of the cornea.

It is preferable to substantially know the ablation rate of stromal tissue for a given system in order to properly shape the stroma, so that optimal ablation can be achieved, while minimizing damage caused by thermal heating of the corneal tissue.

The laser pulse rate is preferably selected to allow the ophthalmologist to perform accurate ablation of the corneal tissue, while at the same time the rate is preferably chosen to be high enough so that the procedure may be performed in a reasonable amount of time. The pulse repetition rate is normally less than about 50 Hz, and preferably the rate is chosen to be greater than about 10 Hz. In preferred embodiments, the pulses are provided at a rate between about 20 and 25 Hz.

As mentioned above, it has been discovered that under certain conditions, photoablation by-products resulting during the PRK procedure can affect the accuracy and the predictability of the procedure.

Figure 3:
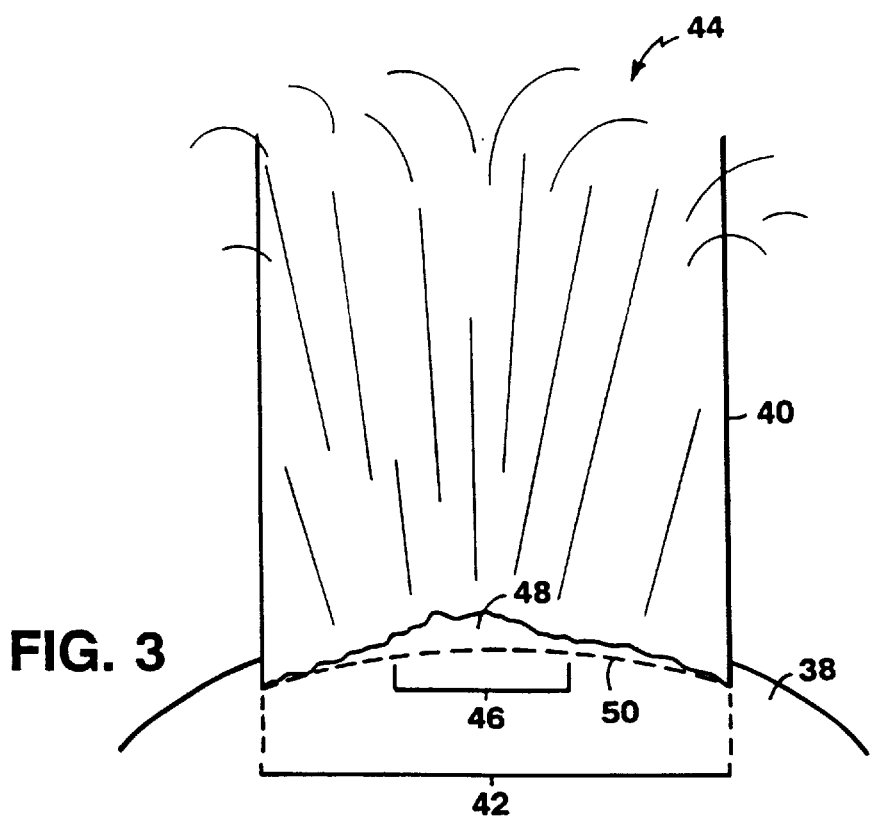
FIG. 3 is a schematic cross-sectional view of a cornea under conventional PRK conditions.

As shown in FIG. 3, during a conventional PRK photoablative shaping of a patient's cornea 38, laser radiation 40 of a known intensity distribution is controllably applied to the surface of the cornea in an ablation area 42. Ablation products (too small to be shown) heat and expand away from the surface of cornea 38 in the form of a plume 44 with very high initial velocities. Pressure differentials developed near the surface of cornea 38 tend to cause the ablation products to redeposit onto the surface of the cornea in the ablation region.

Under conventional PRK conditions, the ablation products can become preferentially deposited in a central portion 46 of ablation area 42, thereby creating a central island 48 of excess material, as compared to the desired corneal shape shown by dotted curve 50.

The dynamics of the plume also appear to non-uniformly affect the removal of material from regions across the surface of the ablation area.

Figure 4:
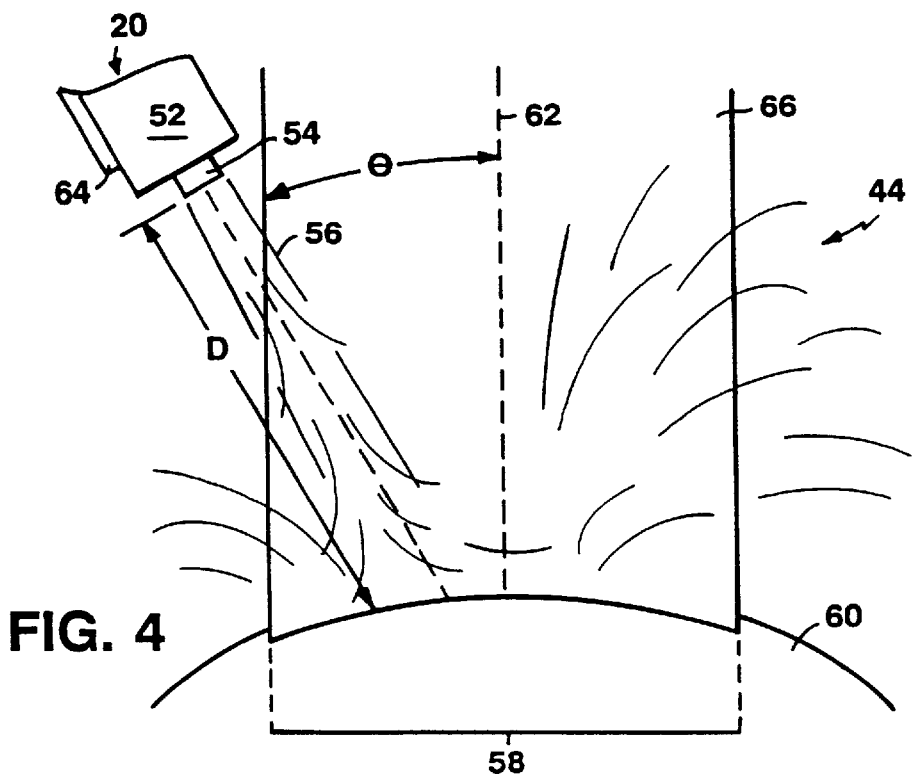
FIG. 4 is a schematic cross-sectional view of a cornea during a PRK procedure according to one aspect of the invention in which humidified gas is delivered continuously to an ablation area.

In one embodiment of the invention, shown in FIG. 4, plume-altering correction device 20 includes a nozzle 52 that has an orifice 54 for directing a flow of a gas 56 (e.g., nitrogen or helium gas) toward an ablation region 58 on the surface of a patient's cornea 60. The orifice has a circular cross-section with a diameter between about 100 $\mu$m and about 1,000 $\mu$m, and is maintained a distance D of about 1 to 5 cm from the surface of ablation region 56.

Gas 56 is delivered to ablation region 58 at a velocity comparable to the velocity at which the ablation products escape from the surface of region 58. Preferably the gas velocity exiting orifice 54 is at least about 120 m/s, and is preferably between about 120 and 200 m/s. Due to boundary and proximity considerations, the actual gas flow rate at the cornea-air boundary is much less, with a lower limit of about 1 m/s at the corneal surface required to prevent the non-linear ablation phenomenon. The gas flow rate is preferably about 10 to 15 liters/minute.

The inventors have discovered that the removal of ablation products from the surface of the ablation region is most effective when nozzle 52 directs gas 56 towards the surface of ablation region 58 at an angle $\theta$ of about 0° to 30° relative to an axis 62 that is normal to the surface of ablation area 58.

It is speculated that by directing gas 56 at such a steep angle relative to the initial direction of escape of the ablation products (i.e., along the normal to the surface of the ablation region), the pressure differentials developed along the surface of the ablation region are favorably altered in a manner substantially reducing the non-uniform material removal effect, caused by either non-uniform redeposition or non-uniform ablation by-product escape.

Gas 56 is humidified by humidifier 64 (e.g., a conventional medical humidifier) to prevent dehydration of the patient's eye. Gas 56 is preferably humidified near the saturation point of the ambient air.

As shown in FIG. 4, gas 56 is delivered continuously to the ablation region during the PRK procedure. The flow of humidified gas is initiated prior to the application of laser pulses 66. As the laser fires and pulses 66 are applied to the ablation region, the continuous gas flow is employed to disturb the dynamics of the plume in such a manner as to prevent the ablation products from returning to the surface of ablation region 58 and to provide a uniform escape for ablation by-products across the surface of the ablation area. At the termination of the application of the laser pulses, the gas flow is discontinued.

The gas may be delivered continuously, as described above, or intermittently in a series of puffs. A continuous flow of gas requires a relatively less complex set-up. However, when the gas is delivered in a pulsed series of puffs, less gas is required for a PRK procedure, and the cornea would be less likely to become dehydrated.

Figure 4A:
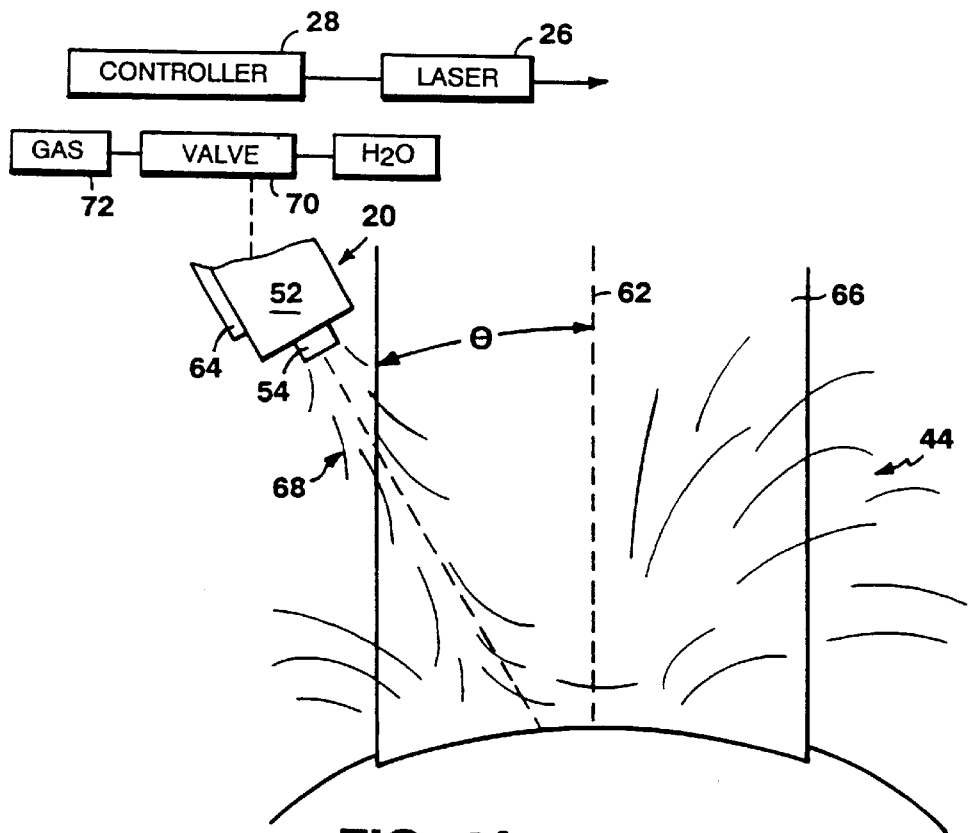
FIG. 4A is a schematic cross-sectional view of a cornea during a PRK procedure according to one aspect of the invention in which humidified gas is delivered intermittently as a series of puffs to an ablation area.

As shown in FIG. 4A, puffs 68 of gas 56 are delivered to the surface of ablation region 58 at times substantially synchronized with the incidence of the pulses of laser radiation 66.

In operation, signals from controller 28 activate a manifold valve 70 between nozzle 52 and a pressurized supply 72 of gas 56 (e.g., $N_2$ or He) to provide gas to the ablation region 5 to 10 milliseconds before each laser pulse 66 to establish a plume-disturbing gas flow before the formation of the plume of ablation products. Typically, the laser pulses have a duration of about 10 nanoseconds. Controller 28 subsequently activates manifold valve 70 to disconnect the supply of gas to the nozzle about 5 to 10 milliseconds after the termination of each laser pulse to prevent use of excess gas between laser pulses 66, which are typically separated by at least 50 milliseconds.

Figure 4B:
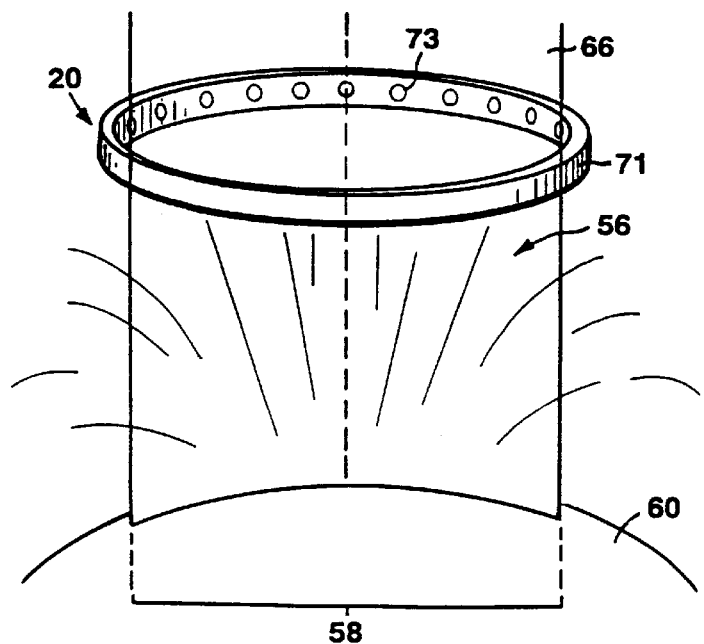
FIG. 4B is a schematic view of a nozzle assembly delivering humidified gas to an ablation area in the cornea of a patient's eye.

Alternatively, as shown in FIG. 4B, correction device 20 includes a nozzle assembly 71 that surrounds a significant portion of the ablation area and introduces the humidified gas 56 to the ablation area from a series of orifices 73 above the surface of the ablation area. Nozzle assembly 71 is preferably in the form of an annular ring, as shown in the drawing.

Figure 5:
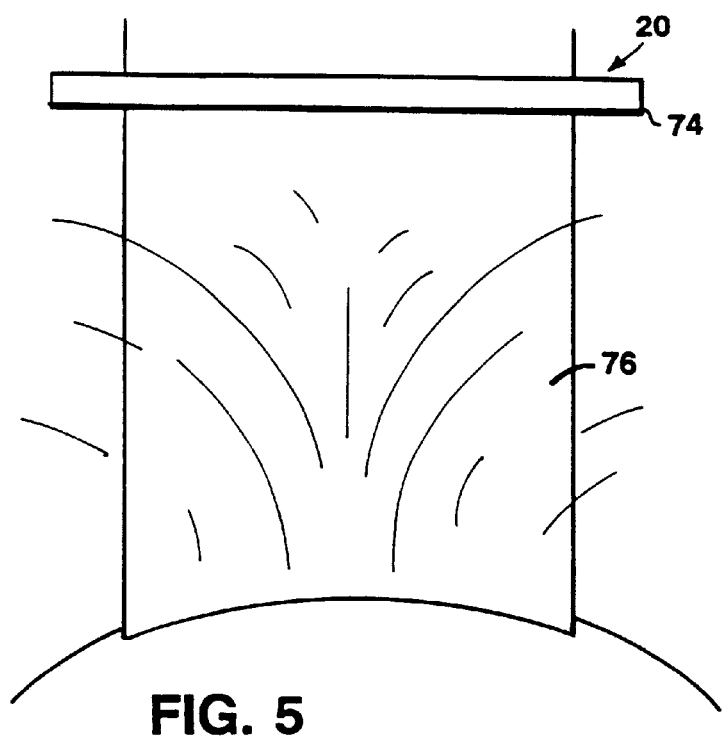
FIG. 5 is a schematic view of a beam intensity defining means delivering photoablating radiation to an ablation area in the cornea of a patient's eye.

In an alternative embodiment, the laser beam itself can be employed to substantially prevent non-uniform material removal. For example, as shown in FIG. 5, correction device 20 includes an optical means 74 (e.g., a lens and an optical attenuator) to selectively control the cross-sectional intensity distribution of radiation pulses 76 to alter the manner in which the ablation products escape from the surface of the eye so as to substantially prevent the ablation products from depositing onto the surface of the ablation region.

The inventors have discovered that the formation of the plume of ablation products can be favorably altered by controlling the intensity distribution of the pulses of photoablative laser radiation to have a higher intensity distribution in the central portion of the ablation region than at the periphery of the ablation area. The intensity distribution is selected to have a predetermined intensity fall-off characteristic from the central portion of the radiation pulses to the periphery. Preferably, the intensity at the periphery of the cross-section intensity distribution is reduced by about 10 to 15% relative to that of the central portion.

It is surmised that the escape of ablation products from the surface of the ablation region, produced by laser pulses with the above non-uniform intensity distribution, has flow directions outside and away from the ablation region. This effect is attributed to the creation of a non-uniform pressure wave above the surface of the ablation area as the corneal tissue is ablating. The laser radiation is shaped to create velocity components away from the surface for the ablation products that are sufficiently strong to substantially prevent the above-mentioned non-uniform material removal effect.

Figure 6:
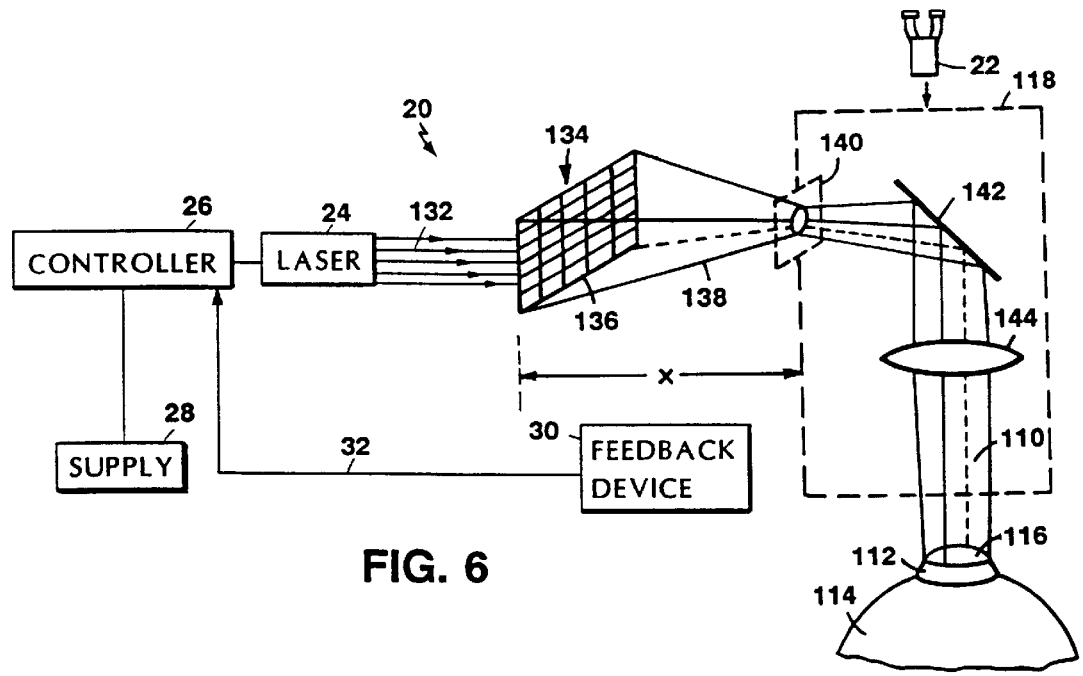
FIG. 6 is a schematic diagram of a beam profiler that modifies an initial laser beam, and a subbeam delivery system that delivers the resulting beam to the corneal surface of a patient's eye.

Referring to FIG. 6, the beam 110 of photoablation radiation can be modified to have an intensity profile across the beam that can produce the desired shape in the cornea surface. The beam profile is selected by initially assuming ideal conditions (i.e., ignoring the material removal effects), the selected profile is then modified to prevent the material removal effects.

As shown in FIG. 6, a beam of photoablating laser radiation 110 that has a predetermined intensity profile, created by a beam profiler in accordance with the present invention, impinges on the corneal surface 112 of a patient's eye in an ablation region 116 to produce a desired refractive correction in the patient's eye.

Profiler 134 divides an initial laser beam 132 into an array of subbeams 138, each having a one-to-one correspondence with a respective portion of the initial beam, and each of which being modified from its respective portion of the initial beam as a result of interacting with a respective profiling element 136, which received that portion of the initial beam, and provides a desired beam-modifying function.

Subbeams 138, modified by profiler 134, are directed to an overlap plane 140, which can correspond to the actual ablation area 116, or preferably, as shown, subbeam delivery system 118 directs individual subbeams 138 over a desired distance from the laser to again overlap at the ablation area that is spaced a certain distance from overlap plane 140.

An aperture 139 (FIG. 6A), or other optical device, is preferably located at the overlap plane to substantially eliminate fringe effects.

In beam profiling according to the invention, rather than attempting to modify the entire beam 132 according to a desired beam intensity profile, each of the profiling elements modifies only a selected portion of beam 132 according to the desired intensity profile. In this way, the intensity variation across any of the profiling elements is less than the intensity variation across the entire beam 132, and upon imaging of the subbeams in overlap plane 140, by optical incoherent summation, the undesired intensity variations in the initial beam become substantially cancelled.

Thus, a beam that has a highly reproducible, predictable and desired intensity profile can be provided which is substantially independent of the intensity variations over the cross-section of the initial laser beam.

Figure 6A:
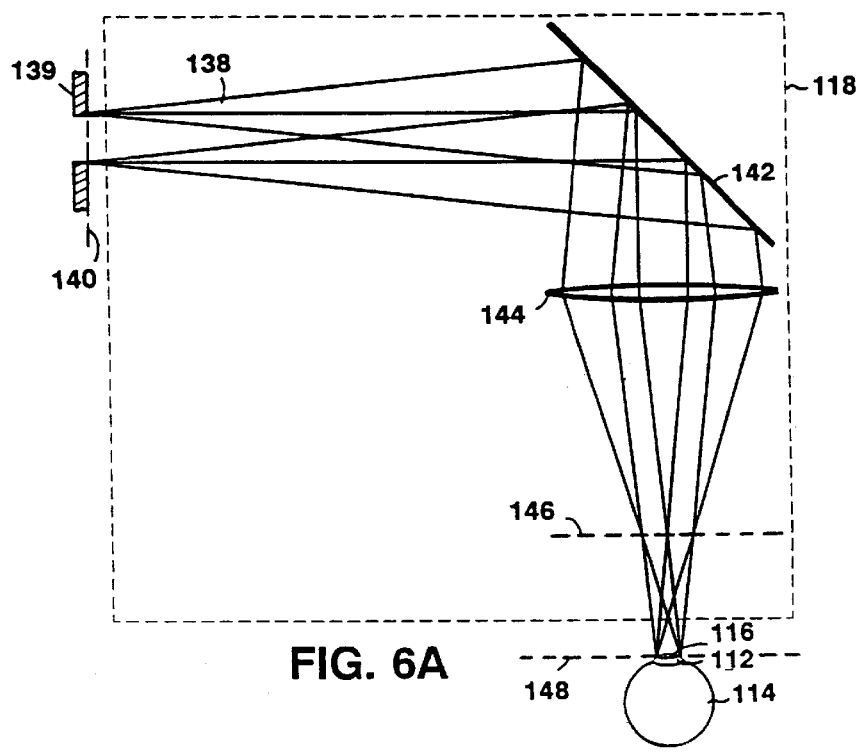
FIG. 6A is a more detailed schematic view of the subbeam delivery system of FIG. 6.

As shown in FIG. 6A, subbeam delivery system 118 includes a mirror 142 and a lens 144 which focuses subbeams 138 onto a focal plane 146 and which also images the subbeams onto an image plane 148 corresponding to ablation area 116.

Subbeam delivery system 118 does not substantially alter the intensity distribution of subbeams 138, thus the intensity profile of each subbeam at overlap plane 140 is substantially the same as the intensity profile of each overlapped subbeam forming photoablating beam 110 at corneal surface 38. Beam 110 applied to the cornea substantially covers the entire ablation area 116, which generally corresponds to the portion of the corneal surface used for eyesight.

It is important that the subbeams 138 substantially overlap in overlap plane 140. This overlap depends, at least in some respects, upon the degree of spatial coherence of initial beam 132 from laser 26, which can be measured by the intrinsic divergence of the beam. Typical excimer lasers (e.g., available from Summit Technologies) provide beams which have an intrinsic divergence of about 1 milli-radian, which provides sufficient coherence to enable operation of the system in important instances.

In preferred embodiments, the distance X between profiler 134 and overlap plane 140 is selected so that the product of the intrinsic divergence of the beam and the distance X is less than the area of subbeam overlap in overlap plane 140, so that the desired level of cancellation of the variation in the initial beam intensity profile. Generally, it is preferred that this product be selected to be less than about 50% of the overlap area, and preferably this product is less than about 5–10% of the overlap area.

In preferred embodiments, the distance X is selected to be large enough so that beam distortions do not occur, such as those distortions which, for correction, would require use of so-called "fast optics."

Figure 6B:
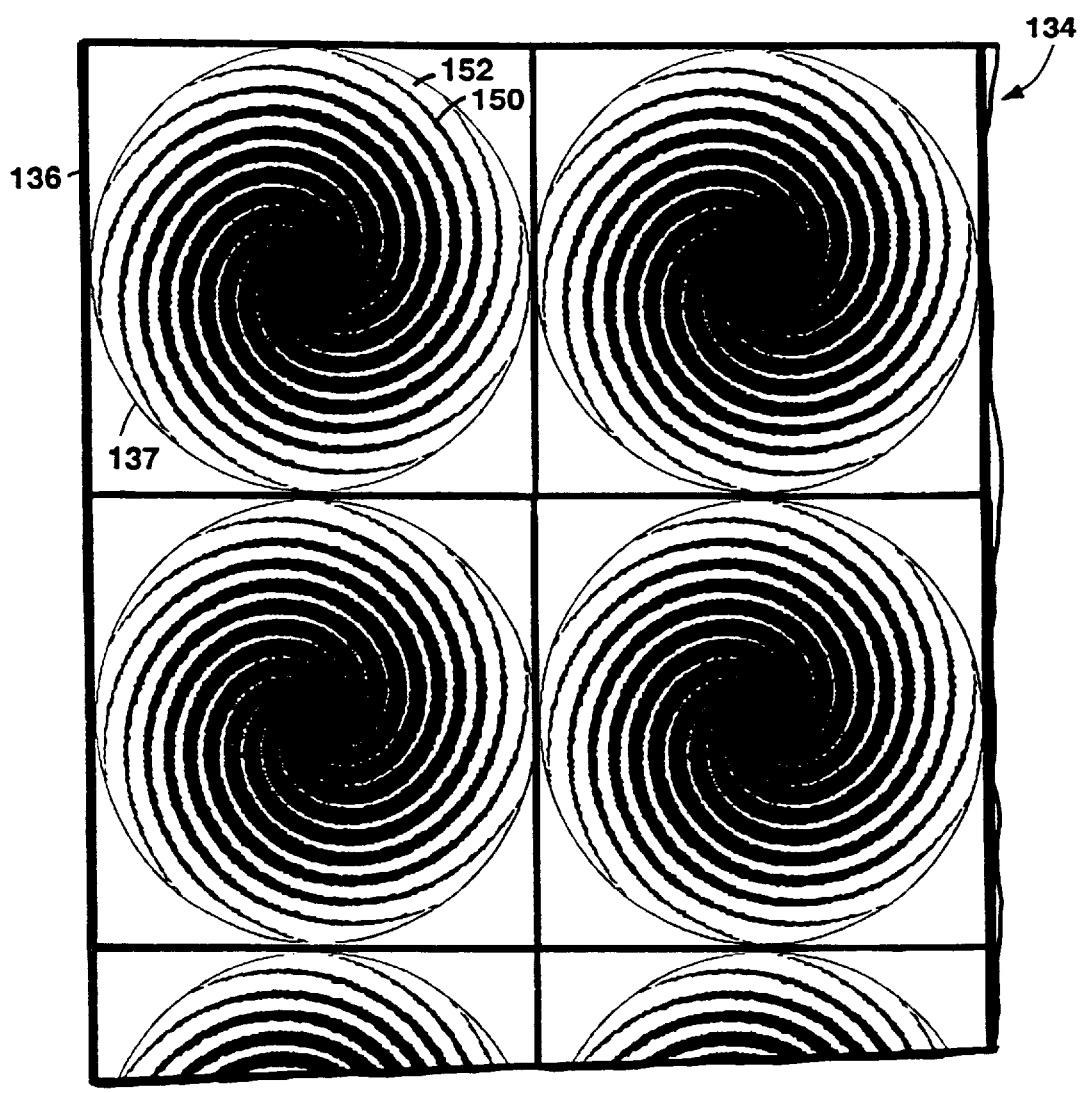
FIG. 6B is a partial schematic view of an array of intensity-defining elements.

As shown in FIGS. 6B and 6C, in preferred embodiments, each optical element 136 includes an intensity-defining element 137 that comprises a predetermined pattern of light-transmissive and non-transmissive regions 150 (shown in black) and 152 (shown in white), respectively.

The predetermined pattern of each optical element is selected to produce the desired intensity profile to permit uniform shaping of the patient's eye by substantially avoiding material removal effects.

The variation in the light intensity of each subbeam depends upon the size of the smallest features of the selected profiling element pattern. For patterns which have relatively small features, the intensity of each resulting subbeam 138 varies smoothly. Whereas for patterns with somewhat larger features, the intensity variation of each resulting subbeam beam 138 is less smooth.

It is desirable that the coarseness (i.e., the feature size) of each profiling element pattern be selected to be small enough so that the respective intensity profile transferred to each subbeam 138 becomes averaged out by the intrinsic divergence of the beam by the time the subbeams reach the overlap plane 140.

For example, for an average feature size of about 2 mm, a beam divergence of 1 milli-radian, and assuming that at least eight of the profiling elements of profiler 134 are employed to achieve proper overlap cancellation of the subbeam artifacts, a distance of at least about 25 to 50 cm, between profiler 134 and overlap plane 140, is preferred.

The patterns of light-transmissive and non-transmissive regions are preferably fabricated by depositing a metal film upon a transparent substrate (e.g., glass or quartz) and defining the pattern of each element 136 by well-known semiconductor device processing techniques (e.g., chemical etching or metallization lift off).

In preferred embodiments, the transparent substrate is constructed out of material that is substantially transmissive to light in the operating wavelength range. For example, for UV laser radiation, the substrate is preferably fabricated from quartz, LiF, CaF, MgF or sapphire, while for visible or infra-red laser radiation, glass or low loss moldable plastic materials are preferably used.

Beam profiler 134 also includes a subbeam-directing optical system 154 for directing each subbeam 138 to overlap plane 140. Two preferred embodiments are shown in FIGS. 6C and 6D.

The subbeam-directing optical system shown in FIG. 6C is implemented as two overlapped arrays of linear prisms 156, 158, which are rotated 90° with respect to each other, and which serve to direct each of the subbeams 138 to overlap plane 140.

Figure 6D:
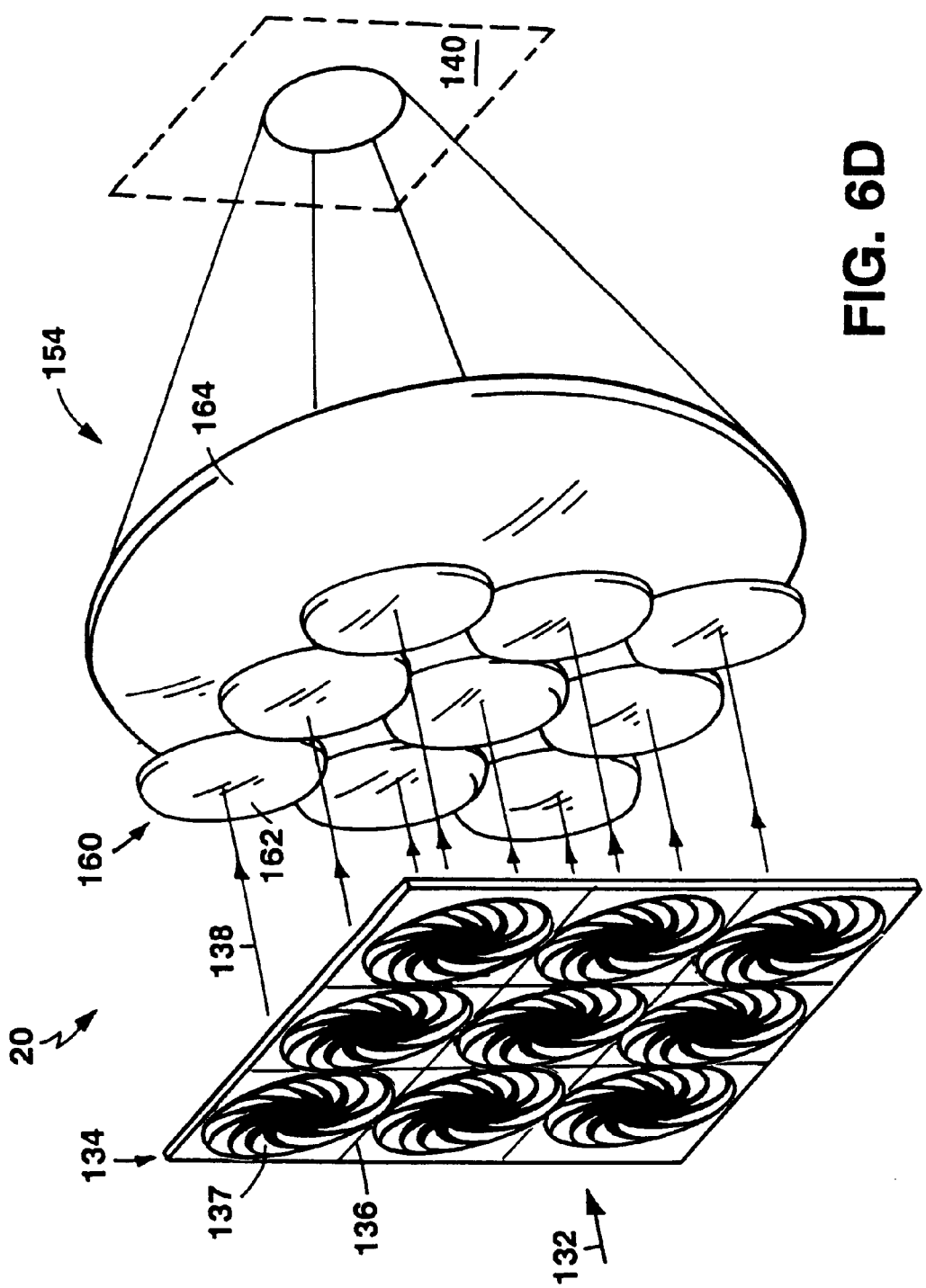
FIG. 6D is a perspective view of a subbeam-directing optical system including an array of lenses and a relatively large lens positioned adjacent the array.

In alternative embodiments, shown in FIGS. 6D, subbeam-directing optical system 154 is implemented as an array 160 of relatively small lenses 162, each having an area about equal to the area of each profiling element 136 and each being located proximal to a respective profiling element 136, and a large focusing lens 164 that has an area large enough to receive each subbeam 138. Lens 164 can be located adjacent to array 160, as shown in FIG. 6D, or alternatively, lens 164 can be located at a distance from array 160 that is about twice the focal distance of each lens 162.

It is to be noted that for the embodiment shown in FIG. 6D, in which lens 164 is adjacent array 160, focusing lens 164 can be located on either side of array 160.

Figure 6E:
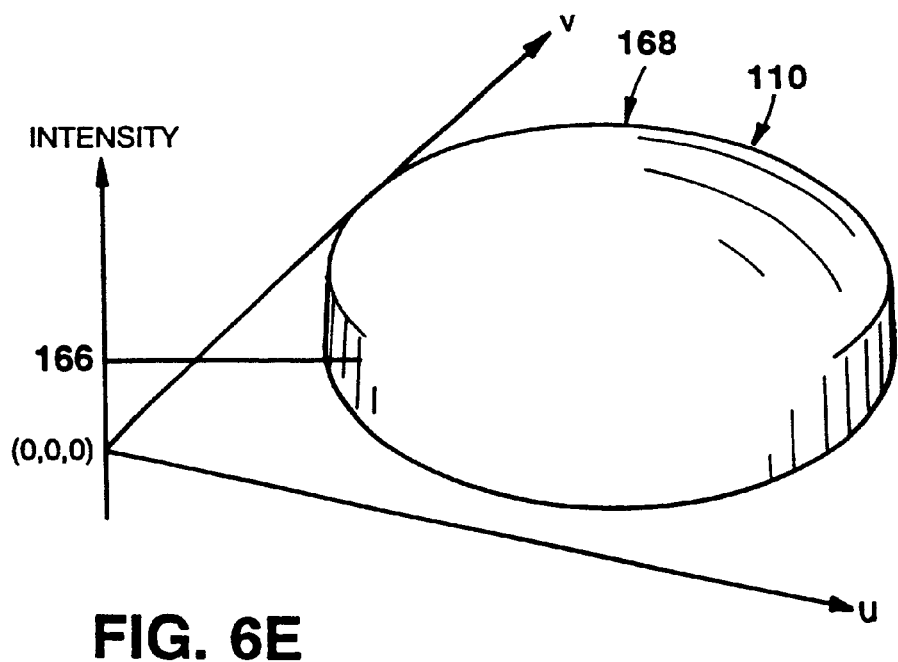
FIGS. 6E and 6F are three-dimensional graphs of intensity profiles of a resulting photoablation beam, created by beam profilers according to the invention, that can be used for treatment of myopia and hyperopia, respectively.
Figure 6F:
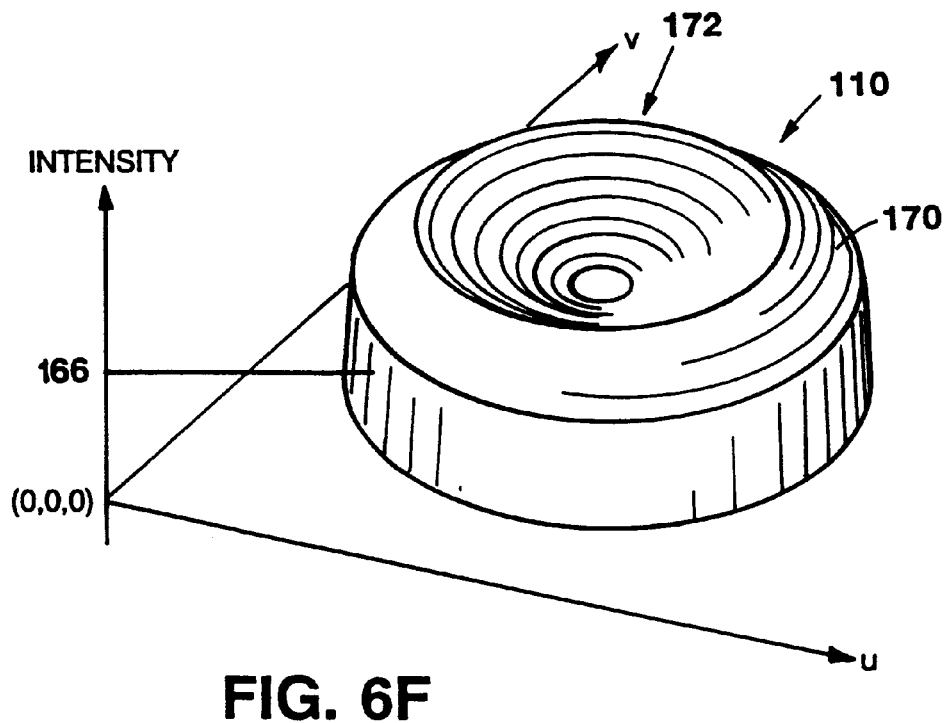

FIGS. 6E and 6F show two selected light intensity profiles of photoablation beam 110, as a function of cross-sectional coordinates (u,v), for photorefractive corrective treatment of myopia and hyperopia, respectively, according to the invention. In these embodiments, photoablation beam 110 typically has, e.g., a circular cross-section and a smoothly varying intensity profile with a selected threshold value 166. Each profile is modified to substantially prevent the above-mentioned non-uniform plume effects.

For the myopic correction (FIG. 6E), the highest light intensity is delivered in the central region 168 of the cornea to cause relative flattening of the corneal surface.

For the hyperopic correction (FIG. 6F), increased ablation is needed in the annular perifocal region to cause an increase in the corneal curvature. Thus, the light intensity distribution has a maximum in an annular region 170 and a local minimum in the central region 172.

Figure 7:
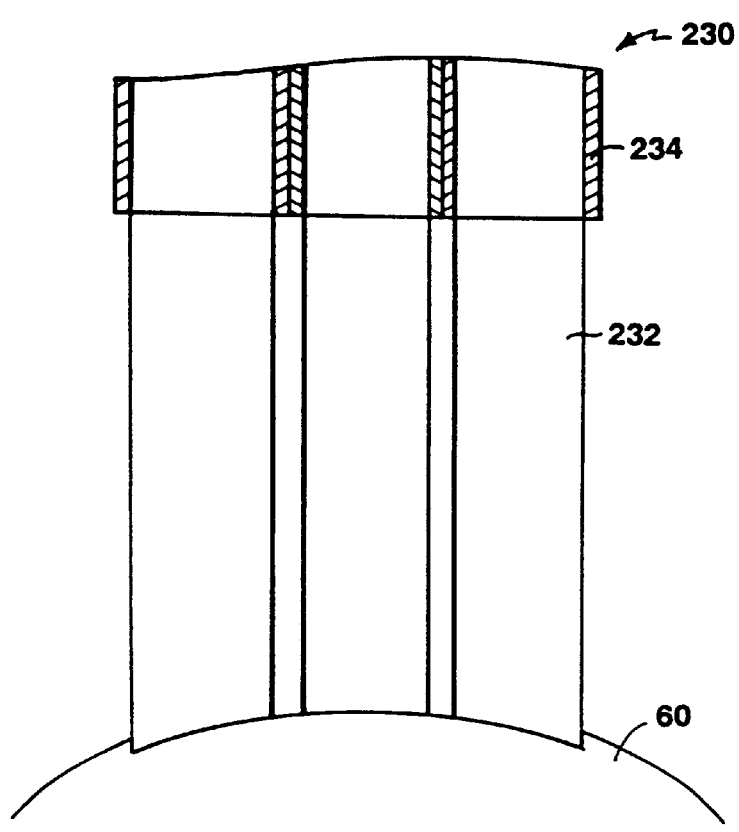
FIGS. 7 and 7A are schematic side and sectional views of a PRK system in which a single beam of photoablative radiation is divided into an array of smaller beams prior to ablating corneal tissue.
Figure 7A:
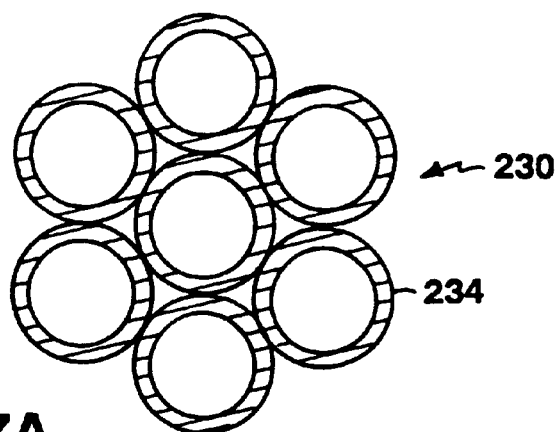

Referring to FIGS. 7 and 7A, in another embodiment, an optical spatial beam modulator 230 divides a single beam of photoablative laser radiation into an array of smaller beams 232. Optical modulator 230 includes a close-packed array of optical waveguides 234 (e.g., pyrex tubes)

Beams 232 are arranged to produce e.g., a close-packed hexagonal ablation region, with each beam being adjacent, but not overlapping, the other beams. Beams 232 are displaced randomly between the pulses of photoablating radiation so as not to produce e.g., a hexagonal pattern in the ablation region.

Beams 232 appear to break up the pattern of ablation that would otherwise exist for a single radiation beam, and produce smaller plumes of ablation products, each of which having a smaller impact on the resultant shape of the flatness of corneal tissue removal. In this way, the variation of deposition over the surface of the ablation region can be reduced.

Figure 8:
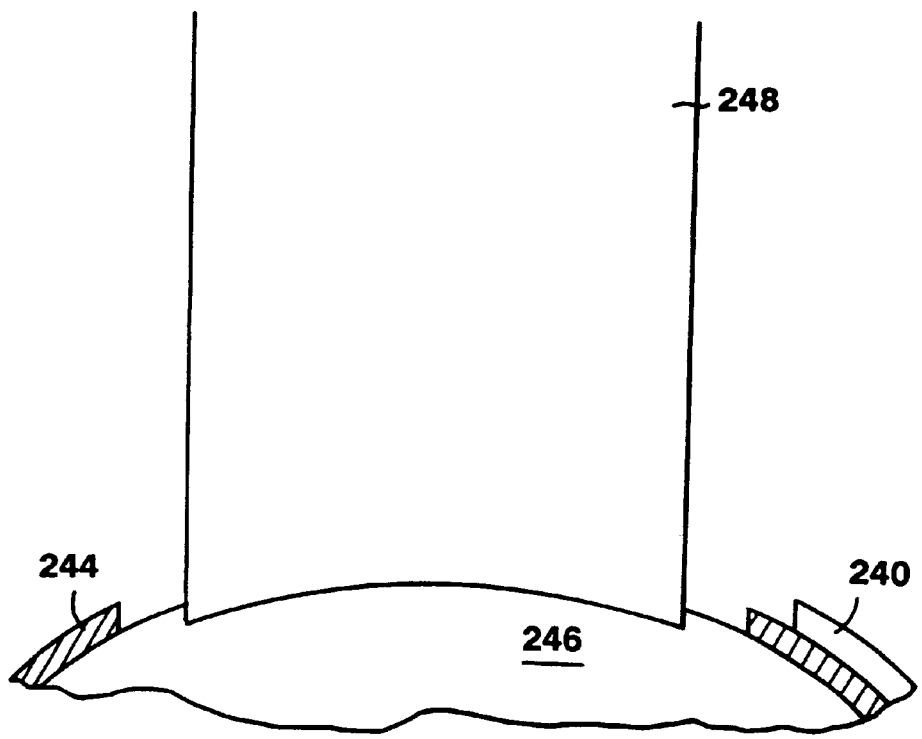
FIG. 8 is a schematic side view of an acoustic transducer that is configured to apply pressure to the surface of the cornea in a region surrounding the ablation area.

Referring to FIG. 8, an acoustical transducer 240 (available from e.g., Panametrics, Inc. of Waltham, Mass.) is used to generate short-pulsed acoustical waves, with frequency on the order of kHz, above the corneal surface, or alternately, on the corneal surface in the vicinity of ablation area 242. Acoustical transducer 240 preferably includes a shroud 244, preferably in the form of an annular ring, to apply pressure to the corneal surface 246.

The generation of acoustical waves serves to break up the symmetry of the ablation process during the onset and the duration of photoablating pulses 248, and shortly thereafter. In other words, the corneal tissue is tapped by the transducer in such a way as to disturb subsequent acoustical pulses generated in the corneal tissue by pulses 76.

It is proposed that the disturbing acoustical waves will alter the formation of the plume dynamics through an acoustic cancellation effect that substantially reduces the non-uniform deposition of the ablation products on the surface of the ablation area.

Transducer 240 is caused to disturb the corneal tissue at times synchronized with the incidence of the photoablating radiation upon the surface of the ablation area. For example, the controller can activate the transducer 5 to 10 ms before the incidence of each of the laser pulses, and turn off the transducer 5 to 10 ms after each of the pulses.

The transducer preferably causes vibrations in the air above the surface of the corneal tissue in magnitudes that are comparable to the pressure dynamics in the plume of ablation products created by the photoablating radiation.

As discussed above, it has been realized that the hydration level of the corneal tissue during the PRK procedure can vary over the ablation area and non-uniformly affect the PRK procedure. The differences in the relative hydration across the ablation area can non-uniformly affect the removal of corneal tissue by photoablation. The inventors have provided a number of schemes for substantially preventing the fluid dynamics of the cornea from causing non-uniform tissue removal.

In one embodiment, the corneal hydration level can be substantially controlled by saturating the ablation area with fluid in a manner maintaining a substantially uniform hydration level in the ablation area during PRK. In preferred embodiments, the corneal hydration level is maintained by continuous misting or by applying drops of water or other similar fluid (e.g., saline) to the ablation area by means of humidifier 64 or an external water nozzle.

The hydration level of the ablation area can also be controlled by optically varying the area on the surface of the ablation area to which the profiled beam pulses are delivered from an initial area of a size substantially corresponding to the size of the ablation area to a final size of relatively smaller size. Fluid may accumulate substantially uniformly in the ablation area because the beam pulses initially ablate tissue corresponding to the entire ablation area. Therefore, the photo-sensitivity will likely remain uniform across the ablation area during most of the PRK procedure, thereby enabling substantially uniform ablation of the corneal surface.

The desired portion of the cornea may be shaped by selectively controlling the shape and size of the irradiated area of the cornea, as described in Marshall et al., U.S. Pat. No. 4,941,093 (assigned to the present assignee), which is incorporated herein by reference.

Preferably photoablating radiation is pulsed repeatedly and using an iris diaphragm, optical stops, mirrors, beam splitters, and other similar devices, the pulses of energy are directed to the epithelial surface so that, over a period of time, different regions of the surface are exposed to different quantities of energy so as to produce the desired differential ablation of the corneal ablation region.

Figure 9:
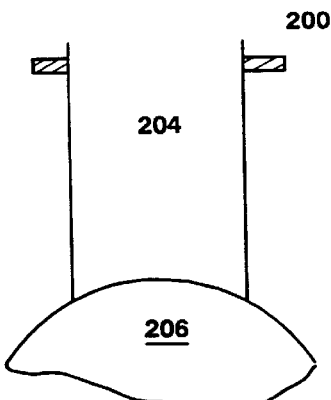
FIG. 9 is a schematic diagram shown in partial cross-section of a device for practicing a method of shaping the cornea employing a variably-sized aperture.

As shown in FIG. 9, aperture 200 is located in the path of laser pulses 204. The size of the aperture controls the area of the surface of the ablation area that will be irradiated by pulses 204. FIGS. 9A–9D illustrate how, by changing the aperture over a period of time during which laser pulses 204 are continually supplied, a cornea 206 may be shaped into the final desired shape.

Figure 9A:
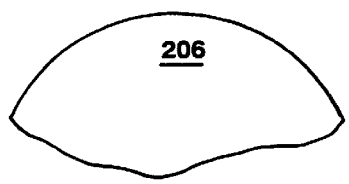
FIGS. 9A–9D are schematic cross-sections of the cornea showing how different profiles may be obtained by altering the size of the area over which laser pulses irradiate the surface of the exposed corneal tissue.
Figure 9B:
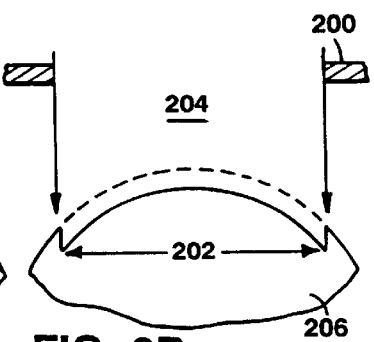
Figure 9C:
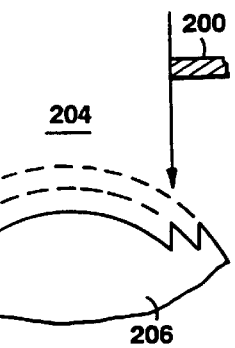
Figure 9D:
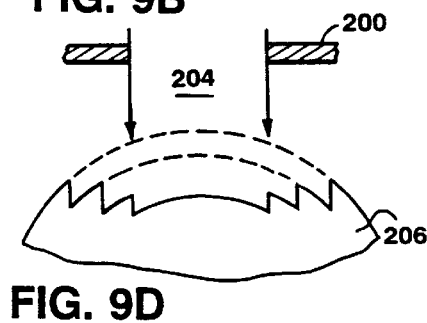

A large area of corneal tissue will be exposed, and thus ablated, with a large aperture (FIG. 9B). If the aperture is then reduced, a smaller area of corneal tissue will be ablated, and changing the profile to that of FIG. 9C. If the dimension of the aperture is further reduced, subsequent laser pulses will ablate an even smaller area of corneal tissue, as shown in FIG. 9D.

A general flattening of the surface, relative to the original surface of FIG. 9A, will result by concentrating laser pulses 204 in the central region of the ablation area to compensate for the additional material added by the deposition of the ablation products.

Alternatively, iris 200 can be disposed between ablation region 202 and the source of laser radiation 204 to compensate for the non-uniform ablation caused by the plume dynamics. The controller adjusts the aperture of iris 200 to account for the non-uniform ablation of corneal tissue by preferentially ablating regions where excess material exists on the surface of the ablation area (e.g., the central portion).

The amount of compensation required to cancel the non-linear ablation phenomenon is on the order of 10% of the overall correction, or about 1 µm/diopter of correction intended which must be additionally removed from the central region (e.g., a circular region with a diameter of about 2–3 mm).

In another embodiment, non-uniform tissue removal phenomena can be compensated for by employing an erodible mask, or other optical attenuator, in conjunction with pulses of laser radiation, as described in Muller, U.S. Pat. No. 4,856,513, and in Raven et al., U.S. Pat. No. 4,994,058, both of which assigned to the present assignee and are incorporated herein by reference.

In this scheme, the erodible mask is designed to selectively transmit radiation from the laser to the ablation area to produce the desired ablation of corneal tissue, including a correction factor based on e.g., the disturbances that are anticipated to occur based upon the type of correction being produced and the parameters of the system.

Figure 10:
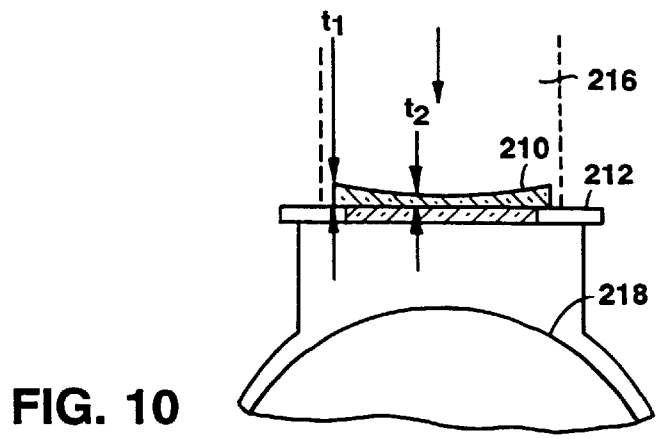
FIG. 10 is a schematic cross-sectional side view of a device for practicing a method of shaping the cornea employing an erodible mask.
Figure 10A:
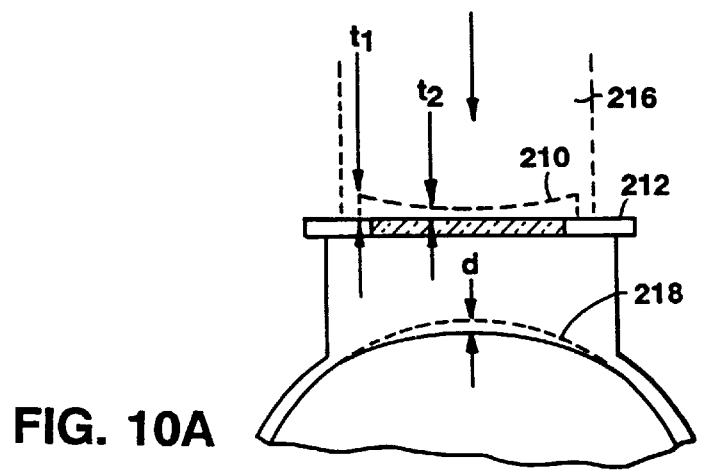
FIG. 10A is a schematic cross-sectional side view of the device in FIG. 10A after the corneal tissue has been shaped.

Referring to FIGS. 10 and 10A, mask 210 is supported by a stage 212 which has a section 214 that is transparent to laser radiation 216. During the irradiation, the mask 210 is gradually eroded, and a larger area of the corneal tissue 218 becomes exposed to the ablating radiation.

As indicated in FIG. 10A, at the moment the mask has been entirely eroded, the surface of the corneal tissue has been ablated in a manner compensating for the deposition of ablation products onto the surface of the ablation area. The maximum thickness $t_1$ of the mask 210 exceeds the minimum thickness $t_2$ by approximately the maximum depth d ablated into the cornea. As mentioned, the initial shape of the mask is selected to compensate for the deposition effect.

In a further embodiment, radiation pulses which have predetermined non-uniform cross-sectional intensity distributions, e.g., as shown in FIGS. 6E and 6F, are employed in combination with a selectively controlled iris, or an erodible mask.

In this scheme, the deposition of the ablation products onto the surface of the ablation area is caused to be uniform. In other words, rather than preventing the deposition of the ablation products entirely, the preferential deposition of the ablation products in the central portion of the ablation area is reduced to minimize the variation (i.e., non-uniformity) of the deposition.

The iris is controlled by an compensating control algorithm inside controller 28.

Figure 11:
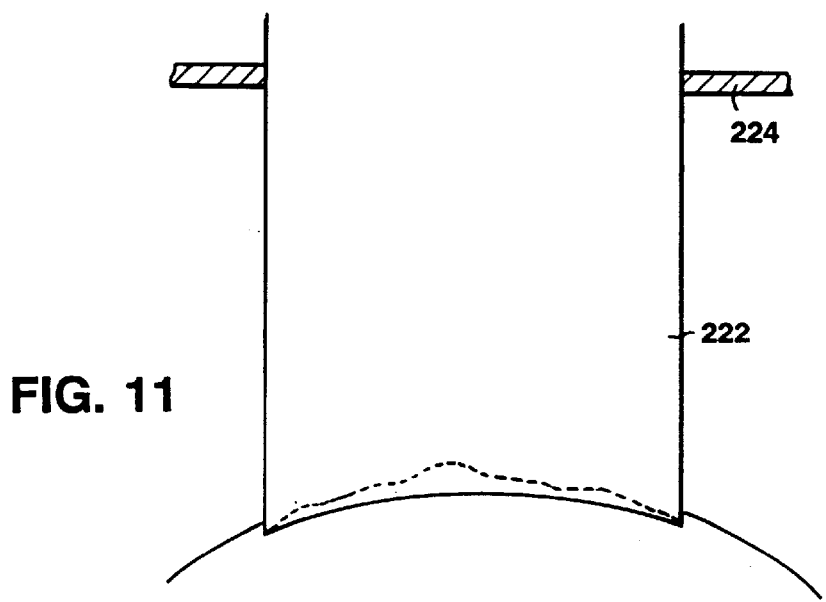
FIG. 11 is a schematic side view, in partial cross-section, of a radiation beam with a non-uniform cross-sectional intensity distribution passing through the aperture of an iris and ablating the surface of a patient's cornea.
Figure 11A:
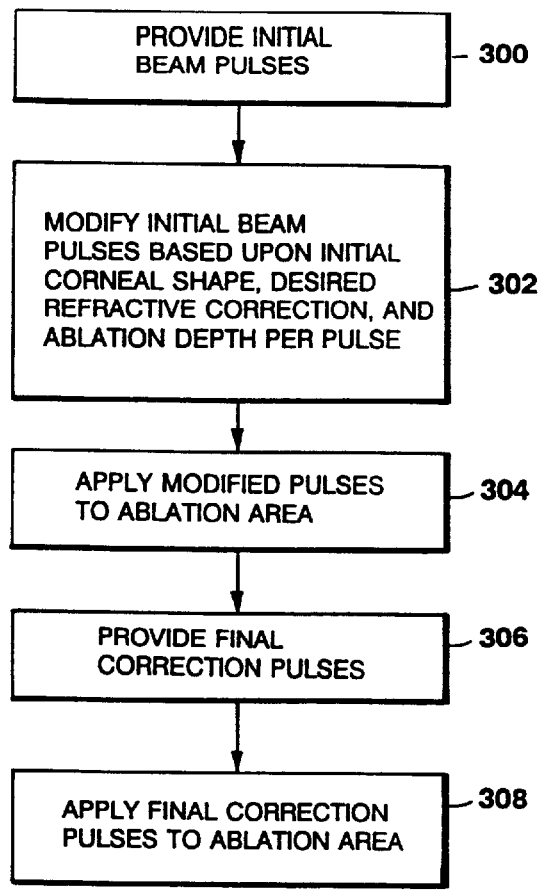
FIG. 11A is a schematic flow diagram for a method for performing PRK according to one aspect of the invention.

As shown in FIGS. 11 and 11A, the excess material in the central region 220 can be removed by using the combination of laser pulses 222, which have a higher intensity in the central portion of the beam than at the edge portion, and an iris 224 that sequentially opens in a manner such that more pulses reach central region 220 than the periphery.

The desired refractive correction can be achieved by a PRK procedure that includes the following steps (FIG. 11A).

The initial beam pulses of photoablating radiation are provided (300). The initial beam pulses are modified to produce respective modified pulses having a modification selected, at least in part, based upon the initial shape of the patient's cornea, the desired refractive correction, and the ablation depth achieved by each of the modified pulses (302). The modified pulses are applied to the ablation area of the patient's cornea (304). The final beam pulses are provided to produce respective final correction pulses for removal of non-uniformly ablated corneal tissue in the ablation area caused by interaction of the modified pulses with ablation by-products resulting from photoablation of the patient's cornea by the modified pulses (306). The modification of the final correction pulses is selected to remove concentration of the photoablation by-products onto the central region of the ablation area. The final correction pulses are applied to the ablation area of the patient's eye, whereby the desired refractive correction is achieved (308).

As discussed above, the inventors have provided a number of schemes for controlling the relative hydration of the patient's cornea in a manner substantially preventing the corneal fluid dynamics in the ablation area from affecting the photoablation of the patient's cornea during the PRK procedure.

In one preferred embodiment, the excess fluid that accumulates in the ablation area is substantially controlled during the during PRK in a manner that prevents the excess fluids from causing non-uniform tissue removal.

In one embodiment according to this scheme, the cross-sectional intensity of the photoablative beam pulses (e.g., from an excimer laser) is attenuated. The intensity of certain of the beam pulses is attenuated below the intensity level required for corneal photoablation, but the intensity is maintained sufficiently high to substantially reduce any excess fluid that may accumulate.

Figure 12:
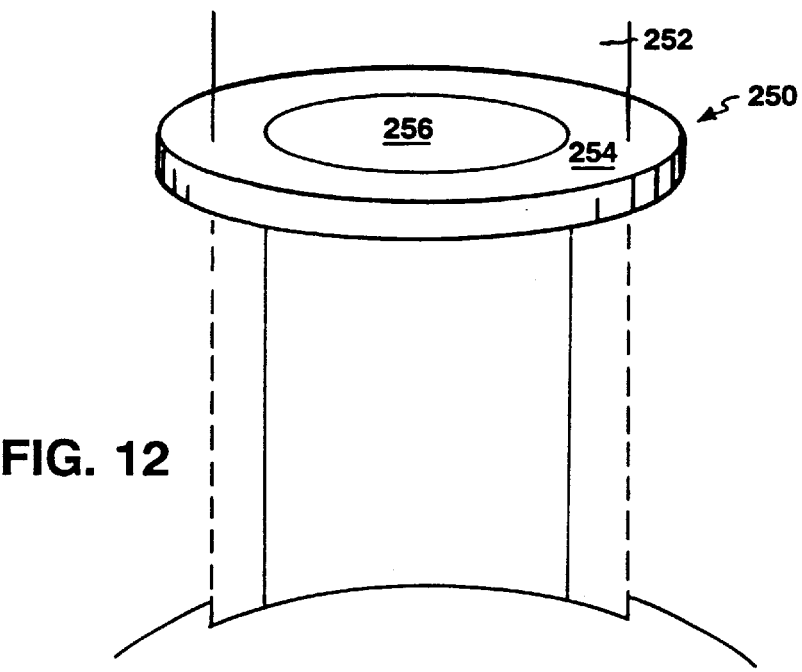
FIG. 12 is a schematic side view of an optical attenuator interposed in the beam path of photoablating radiation during a PRK procedure.

Referring to FIG. 12, an optical attenuator 250 (e.g., an annular ring of glass) is interposed in the beam path of radiation pulses 252 to selectively reduce the cross-sectional intensity of pulses 252 through periphery regions 254 of the attenuator, where the non-uniform deposition of the ablation products is less, relative to central region 256 of the attenuator.

Alternatively, a source of pulses of infra-red radiation of a wavelength selected to correspond with a peak in the wavelength-absorption profile of water can be employed to substantially reduce the excess water accumulation in the ablation area during the PRK procedure. Preferably the pulses of infra-red radiation have a fluence of 1 mJ/cm$^2$ and have a wavelength between about 1 to 12 $\mu$m, and more preferably in the ranges of about 1.4 to 3.2 $\mu$m and 9 to 11 $\mu$m. The infra-red pulses can be shaped to substantially correspond to the central region of the ablation area. The pulses of infrared radiation are preferably delivered in a sequence that alternates with the incidence of the photoablative beam pulses on the surface of the ablation area.

Figure 12A:
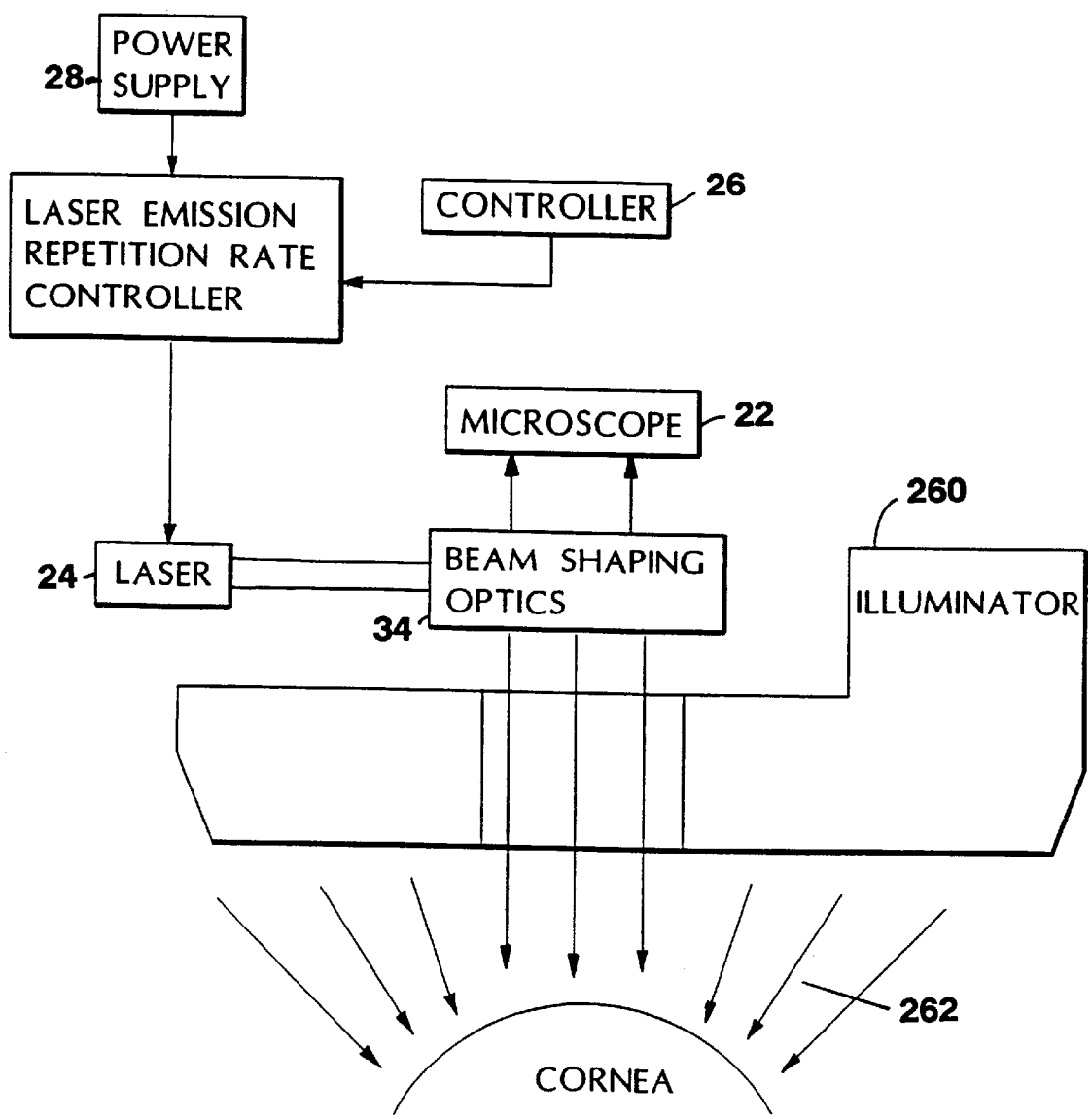
FIG. 12A is a schematic side view of a PRK system employing ocular fluid controlling illumination.

As shown in FIG. 12A, the hydration uniformity across the ablation area can be controlled by applying controlled heating to the anterior surface by using a source 260 of illumination 262 having a sufficient intensity and a wavelength selected to be preferentially absorbed by the anterior 100 $\mu$m of corneal tissue. The power intensity of illumination 262 is preferably selected to be 10 mW cm$^{-2}$, or greater.

In another embodiment, the corneal tissue in the ablation region can be divided into multiple zones based upon the location of the deposited ablation products, and each zone can be ablated independently in order to compensate for the deposition effect.

It should be noted that further preferred embodiments employ selected combinations of the above-described schemes, depending upon the parameters of the system, in order to avoid non-uniform material removal problems. The combinations are selected to achieve more predictable and accurate results.

In certain embodiments, drugs are topically applied to the cornea to regulate and reduce the release of corneal fluids so as to control the uniformity of corneal hydration during PRK. Preferred ocular fluid-controlling drugs include phenol-barbital and carbonic-anhydrase inhibitors such as acetazolamide which has a 30% suppression of fluid proliferation.

Other embodiments are within the scope of the claims.

What is claimed is:

1. A photo-refractive keratectomy system for producing a desired refractive correction in an ablation area in a cornea of a patient's eye comprising:
   a source of a beam of photoablating radiation capable of ablating the cornea of the patient's eye during a photo-refractive keratectomy procedure; and
   a humidified gas flow producer, disposed between the source and the ablation area, for removing material from a surface of the ablation area in a manner substantially preventing a plume of ablation products produced by the photoablating radiation from causing non-uniform ablation of the patient's cornea, by producing a plume-altering flow of humidified gas through an orifice as a series of intermittent puffs of the gas and at a velocity sufficient to substantially prevent non-uniform ablation of the patient's cornea, the puffs being delivered to the ablation area at a plurality of times substantially synchronized with an incidence of the photoablating radiation upon the ablation area.

2. A photo-refractive keratectomy system for producing a desired refractive correction in an ablation area in a cornea of a patient's eye comprising:
   a source of a beam of photoablating radiation capable of ablating the cornea of the patient's eye during a photo-refractive keratectomy procedure; and
   a humidified gas flow producer, disposed between the source and the ablation area, for removing material from a surface of the ablation area in a manner substantially preventing a plume of ablation products produced by the photoablating radiation from causing non-uniform ablation of the patient's cornea, by producing a plume-altering flow of humidified gas through an orifice at a velocity sufficient to substantially prevent non-uniform ablation of the patient's cornea, the humidified gas flow producer having a nozzle assembly surrounding a significant portion of the ablation area, the nozzle assembly being arranged to simultaneously introduce the humidified gas to the ablation area from a plurality of different locations above the ablation area.

3. A photo-refractive keratectomy system for producing a desired refractive correction in an ablation area in a cornea of a patient's eye comprising:
   a source of a beam of photoablating radiation capable of ablating the cornea of a patient's eye during a corneal reprofiling procedure; and
   an acoustic device disposed near the ablation area for modifying a formation of a plume of ablation products produced by the photoablating radiation in a manner substantially preventing the plume from causing non-uniform ablation of the patient's cornea by producing a plurality of localized acoustic waves proximal to the ablation area that substantially prevent non-uniform ablation with the patient's cornea.

4. The system of claim 3 wherein the acoustic device further comprises a shroud surrounding the ablation area, the shroud being constructed and arranged to produce an acoustic wave in the ablation area in a manner altering a plurality of formation dynamics of the plume of ablation products.

5. The system of claim 3 wherein the acoustic device further comprises a shroud surrounding the ablation area, the shroud being constructed and arranged to produce an acoustic wave in the air proximal to the ablation area in a manner altering a plurality of formation dynamics of the plume of ablation products.

6. The system of claim 3 wherein the acoustic device is constructed and arranged to be activated at a plurality of times synchronized with an incidence of the photoablating radiation upon the ablation area.

7. The system of claim 3 further comprising:
   a mask disposed between the photoablating radiation source and the ablation area, the mask having a pre-determined profile of resistance to erosion by the photoablating radiation, the pre-determined profile being selected to vary a total optical energy received across the surface of the ablation area during the corneal reprofiling procedure in a manner for producing the desired refractive correction in the patient's cornea.

8. The system of claim 3 further comprising:
   a hydration controller for controlling a relative hydration of the patient's cornea.

9. The system of claim 3 further comprising:
   an optical beam shaper disposed between the photoablating radiation source and the ablation area for optically varying an illuminated portion of a surface of the ablation area while maintaining a substantially constant photoablating radiation energy per unit illuminated area during the corneal reprofiling procedure.

10. The system of claim 9 wherein the optical beam shaper further comprises an iris having an aperture for shaping the beam by passage therethrough.

11. A photo-refractive keratectomy system for producing a desired refractive correction in an ablation area in a cornea of a patient's eye comprising:
   a source of a beam of photoablating radiation capable of ablating the cornea of a patient's eye during a photo-refractive keratectomy procedure; and
   a humidified gas flow producer, disposed between the source and the ablation area, for removing material from a surface of the ablation area in a manner substantially preventing a plume of ablation products produced by the photoablating radiation from causing non-uniform ablation of the patient's cornea, by producing a plume-altering flow of humidified gas through an orifice at a velocity sufficient to substantially prevent non-uniform ablation of the patient's cornea, and a flow rate of at least about 10 l/min.

12. The photo-refractive keratectomy system of claim 11 further comprising a profiler disposed between the source and the patient's cornea for profiling a cross-sectional intensity profile of the beam to produce a substantially predetermined ablation profile across a surface of the patient's cornea in the ablation area.

13. The photo-refractive keratectomy system of claim 11 wherein a velocity of the humidified gas flow at a surface of the ablation area is greater than about 1 m/s.

14. A photo-refractive keratectomy system for producing a desired refractive correction in an ablation area in a cornea of a patient's eye comprising:
   a source of a beam of photoablating radiation capable of ablating the cornea of the patient's eye during a photo-refractive keratectomy procedure; and
   a humidified gas flow producer, disposed between the source and the ablation area, for removing material from a surface of the ablation area in a manner substantially preventing a plume of ablation products produced by the photoablating radiation from causing non-uniform ablation of the patient's cornea, by producing a plume-altering flow of humidified gas through an orifice at a velocity sufficient to substantially prevent non-uniform ablation of the patient's cornea, the orifice being arranged to deliver the flow of humidified gas to the ablation area at an angle of about 0 degrees to about 30 degrees relative to an axis normal to a center point of the surface of the ablation area.

15. A photo-refractive keratectomy system for producing a desired refractive correction in an ablation area in a cornea of a patient's eye comprising:
   a source of a beam of photoablating radiation capable of ablating the cornea of the patient's eye during a photo-refractive keratectomy procedure; and
   a humidified gas flow producer, disposed between the source and the ablation area, for removing material from a surface of the ablation area in a manner substantially preventing a plume of ablation products produced by the photoablating radiation from causing non-uniform ablation of the patient's cornea, by producing a plume-altering flow of humidified gas through an orifice at a velocity at the orifice of at least about 100 meters per second to substantially prevent non-uniform ablation of the patient's cornea, the orifice arranged between about 1 cm to about 5 cm from the ablation area.

16. A method for producing a desired refractive correction in an ablation area in a cornea of a patient's eye comprising the steps of:
   providing a beam of photoablating radiation;
   illuminating and ablating the patient's cornea with the radiation; and
   removing material from a surface of the ablation area in a manner substantially preventing a plume of ablation products resulting from the illuminating and ablating step from causing non-uniform ablation of the patient's cornea, by producing a plume-altering flow of humidified gas through an orifice as a series of intermittent puffs of the gas and at a velocity sufficient to substantially prevent non-uniform ablation of the patient's cornea, the puffs being delivered to the ablation area at a plurality of times substantially synchronized with an incidence of the photoablating radiation upon the ablation area.

17. A method for producing a desired refractive correction in an ablation area in a cornea of a patient's eye comprising the steps of:
   providing a beam of photoablating radiation;
   illuminating and ablating the patient's cornea with the radiation; and
   removing material from a surface of the ablation area in a manner substantially preventing a plume of ablation products resulting from the illuminating and ablating step from causing non-uniform ablation of the patient's cornea, by producing a plume-altering flow of humidified gas through an orifice at a velocity sufficient to substantially prevent non-uniform ablation of the patient's cornea, wherein the humidified gas is simultaneously introduced to the ablation area from a plurality of different locations above the ablation area.

18. A method for producing a desired refractive correction in an ablation area in a cornea of a patient's eye comprising the steps of:
   providing a beam of photoablating radiation;
   illuminating and ablating the patient's cornea with the radiation; and
   removing material from a surface of the ablation area in a manner substantially preventing a plume of ablation products resulting from the illuminating and ablating step from causing non-uniform ablation of the patient's cornea by producing a plume-altering flow of humidified gas through an orifice at a velocity sufficient to substantially prevent non-uniform ablation of the patient's cornea, and a flow rate of at least about 10 l/min.

19. The method of claim 18 further comprising:
   profiling a cross-section of the beam to produce a substantially predetermined ablation profile across the surface of the patient's cornea in the ablation area.

20. The method of claim 18 wherein the step of removing material further comprises producing the humidified gas at the surface of the ablation area at a velocity of greater than about 1 m/s.

21. A method for producing a desired refractive correction in an ablation area in a cornea of a patient's eye comprising the steps of:
   providing a beam of photoablating radiation;
   illuminating and ablating the patient's cornea with the radiation; and removing material from the surface of the ablation area in a manner substantially preventing a plume of ablation products resulting from the illuminating and ablating step from causing non-uniform ablation of the patient's cornea, by producing a plume-altering flow of humidified gas through an orifice at a velocity sufficient to substantially prevent non-uniform ablation of the patient's cornea, the orifice being arranged to deliver the flow of humidified gas to the ablation area at an angle of about 0 degrees to about 30 degrees relative to an axis normal to a center point of the surface of the ablation area.

22. A method for producing a desired refractive correction in an ablation area in a cornea of a patient's eye comprising the steps of:

providing a beam of photoablating radiation;

illuminating and ablating the patient's cornea with the radiation; and removing material from a surface of the ablation area in a manner substantially preventing a plume of ablation products resulting from the illuminating and ablating step from causing non-uniform ablation of the patient's cornea, by producing a plume-altering flow of humidified gas through an orifice at a velocity at the orifice of at least about 100 meters per second to substantially prevent non-uniform ablation of the patient's cornea, the orifice arranged between about 1 cm to about 5 cm from the ablation area.

23. A method for producing a desired refractive correction in an ablation area in a cornea of a patient's eye comprising the steps of:

providing a beam of photoablating radiation;

illuminating and ablating the patient's cornea with the radiation beam during a corneal reprofiling procedure; and modifying a formation of a plume of ablation products resulting from the illuminating and ablating step in a manner substantially preventing the plume from causing non-uniform ablation of the patient's cornea by producing a plurality of localized acoustic waves proximal to the ablation area that substantially prevent non-uniform ablation of the patient's cornea.

24. The method of claim 23 wherein the modifying step further comprises synchronizing a delivery of acoustic waves with an incidence of the photoablating radiation upon the ablation area.

25. The method of claim 23 further comprising:

optically varying an illuminated portion of a surface of the ablation area while maintaining a substantially constant photoablating radiation energy per unit illuminated area during the corneal reprofiling procedure.

26. The method of claim 23 further comprising:

controlling a relative hydration of the patient's cornea in a manner substantially preventing a plurality of corneal dynamics in the ablation area from causing a non-uniform ablation of the patient's cornea.

* * * * *